(12) United States Patent
Travis

(10) Patent No.: US 9,173,867 B2
(45) Date of Patent: Nov. 3, 2015

(54) TREATMENT OF IMMUNE DYSREGULATION USING CANNABINOID DERIVATIVES

(71) Applicant: Immugen Pharmaceuticals, Inc., Miami, FL (US)

(72) Inventor: Craig Travis, Miami, FL (US)

(73) Assignee: IMMUGEN PHARMACEUTICALS, INC., Miami, FL (US)

(*) Notice: Subject to any disclaimer, the term of this patent is extended or adjusted under 35 U.S.C. 154(b) by 0 days.

(21) Appl. No.: 14/010,729

(22) Filed: Aug. 27, 2013

(65) Prior Publication Data

US 2014/0066497 A1    Mar. 6, 2014

Related U.S. Application Data

(60) Continuation of application No. 13/555,195, filed on Jul. 23, 2012, now abandoned, which is a division of application No. 11/978,344, filed on Oct. 29, 2007, now abandoned, which is a continuation of application No. 10/328,242, filed on Dec. 22, 2002, now Pat. No. 7,105,685, which is a continuation of application No. 09/928,683, filed on Aug. 13, 2001, now Pat. No. 6,566,560, which is a continuation-in-part of application No. 09/533,386, filed on Mar. 22, 2000, now Pat. No. 6,274,635.

(60) Provisional application No. 60/125,674, filed on Mar. 22, 1999, provisional application No. 60/151,595, filed on Aug. 30, 1999.

(51) Int. Cl.

| A61K 31/353 | (2006.01) |
|---|---|
| A61K 31/352 | (2006.01) |
| A61K 31/05 | (2006.01) |
| A61K 31/09 | (2006.01) |
| C07C 39/08 | (2006.01) |
| C07C 39/10 | (2006.01) |
| C07C 39/19 | (2006.01) |
| C07C 39/24 | (2006.01) |
| C07C 43/23 | (2006.01) |
| C07F 9/12 | (2006.01) |

(52) U.S. Cl.
CPC ............... *A61K 31/352* (2013.01); *A61K 31/05* (2013.01); *A61K 31/09* (2013.01); *A61K 31/353* (2013.01); *C07C 39/08* (2013.01); *C07C 39/10* (2013.01); *C07C 39/19* (2013.01); *C07C 39/245* (2013.01); *C07C 43/23* (2013.01); *C07F 9/12* (2013.01)

(58) Field of Classification Search
CPC .................................................... A61K 31/353
USPC ........................................................ 514/454
See application file for complete search history.

(56) References Cited

U.S. PATENT DOCUMENTS

| 6,274,635 | B1 | 8/2001 | Travis | |
|---|---|---|---|---|
| 6,541,510 | B2 | 4/2003 | Travis | |
| 6,566,560 | B2 | 5/2003 | Travis | |
| 7,105,685 | B2 | 9/2006 | Travis | |
| 8,586,767 | B2 * | 11/2013 | Travis | 549/390 |
| 2007/0179135 | A1 | 8/2007 | Travis | |
| 2008/0108647 | A1 | 5/2008 | Travis | |
| 2012/0122917 | A1 | 5/2012 | Travis | |
| 2012/0289589 | A1 | 11/2012 | Travis | |

FOREIGN PATENT DOCUMENTS

| WO | WO 94/12667 | * | 6/1994 |
|---|---|---|---|
| WO | WO 99/53917 | * | 10/1999 |

OTHER PUBLICATIONS

Huff, Joel R., Journal of Medicinal Chemistry, vol. 34, No. 8, Aug. 1991, pp. 2305-2314.*
U.S. Appl. No. 60/125,674, filed Mar. 22, 1999, Travis.
U.S. Appl. No. 60/151,595, filed Aug. 30, 1999, Travis.
U.S. Appl. No. 11/978,344, filed Oct. 29, 2007, Travis.
Brhat Nighantu Ratnakara vol. -4 (Part VII), 05 (p. 04-08) (Ref. p. 169), edn. 1997, Khemaraja Srikrsnadas Prakasana, Mumbai-4, India.†
Srisankara, Rasacandansu OR Rasaratnasamgrahah, 05 (p. 09-13) (Ref.p. 487-488), 2nd Edn.1928, Yagneshwar Gopal Dixit; Book seller, Budhwaar Peth, Pune, India.†
Govinda Dasa, Bhaisajya Ratnavali, 06 (pp. 14-19) (Ref. p. 104), Edn. 14th, 2001, Chaukhamba Sanskrit Sansthan, Varanasi, India.†

\* cited by examiner
† cited by third party

*Primary Examiner* — Rebecca Anderson
(74) *Attorney, Agent, or Firm* — Novak Druce Connolly Bove + Quigg LLP

(57) ABSTRACT

This invention discloses cannabinoid derivatives and pharmaceutical uses thereof.

1 Claim, No Drawings

TREATMENT OF IMMUNE DYSREGULATION USING CANNABINOID DERIVATIVES

CROSS REFERENCE TO RELATED APPLICATIONS

This is a continuation of U.S. patent application Ser. No. 13/555,195 filed on Jul. 23, 2012, which is a divisional application of U.S. patent application Ser. No. 11/978,344 filed on Oct. 29, 2007, which is a continuation of U.S. patent application Ser. No. 10/328,242 (now U.S. Pat. No. 7,105,685), filed Dec. 22, 2002, which is a continuation of application Ser. No. 09/928,683 (now U.S. Pat. No. 6,566,560) filed on Aug. 13, 2001, which is a continuation-in-part of U.S. patent application Ser. No. 09/533,386 (now U.S. Pat. No. 6,274,635) filed on Mar. 22, 2000, which claims priority to U.S. provisional patent application Nos. 60/125,674 and 60/151,595 filed on Mar. 22, 1999 and Aug. 30, 1999, respectively.

BACKGROUND OF THE INVENTION

The retroviral Human Immunodeficiency Viruses (HIV) 1 and 2 are the most common causative agents of AIDS. Through a portion of a viral envelope protein (gp120), HIV binds specifically and with high affinity to the CD4 molecule on T-lymphocytes. Following binding, the virus fuses with the cell membrane and is internalized. Within the cell, it produces a reverse transcriptase which transcribes its genomic RNA to DNA. The reverse HIV transcript is then integrated into the cellular DNA where it exists for the life of the cell as a "provirus." The provirus can remain latent for an indefinite period of time, or it can be "activated" to transcribe mRNA and genomic RNA, leading to protein synthesis, assembly, new virion formation, budding of virus from the cell surface, and cell death.

While the precise events triggering activation are poorly understood, they appear to lead to liberation or production of endogenous cellular factors that interact with the HIV genome to promote translation. In this regard, binding of cellular SP1 to the HIV promoter (which contains several tandem SP1 consensus binding sites) is needed for high-level transcription of the latent HIV genome. Additionally, NFκB functions as a potent transcriptional activator when it binds to one or two (depending on the HIV strain) consensus binding sites in the HIV enhancer, which is adjacent to the promoter. The transcription factors CREB/ATF, NF-AT, and AP1 also potentiate HIV transcription. As for all retroviruses, the structural and enzymatic gag, pol and env gene products are produced when the provirus is activated. HIV first transcribes gag-pol as a fusion protein which is ultimately cleaved by the HIV protease enzyme to yield the mature viral proteins. HIV also employs additional regulatory proteins (specifically the tat and rev gene products) as transcriptional enhancers to induce high levels of gene expression. Nef is another HIV gene that modulates viral replication levels.

While the set of factors triggering active viral replication remains only partially understood, some of them include heat shock, ultraviolet radiation, regulatory proteins of other (e.g., superinfecting) viruses, inflammatory cytokines (e.g., IL1, IL2, IL4, IL6, IL10, Tumor Necrosis Factor a (TNFα), Platelet Activating Factor, Interferon γ (IFNγ)), and Nitric Oxide. Many of these factors are T-cell activators (e.g., they precipitate cell cycling and clonal expansion of T-cell populations), and they are released by many B-cells in direct response to infectious agents (such as HIV). Such factors also trigger intracellular signaling events promoting the production of NFκB and its dissociation from its inhibitor (IkB). Active NFκB is a DNA binding protein activating the transcription of many cellular genes, and also the HIV genome. In this regard, cytokines such as TNF α and IL-1 augment NFκB activity in cultured T-cells.

Some cells harboring the provirus express HIV gp41, gp120, and possibly other viral proteins, presumably through basal levels of transcription from the proviral genome. While a host immune response is mounted against such HIV proteins, due in part to the high degree of mutability of such proteins and their varied glycosylation patterns, such immune response usually is incomplete, resulting in a pool of latent virus that effectively avoids immune surveillance. Additionally, the presence of HIV gp120 in the membranes of infected cells can mediate fusion events between infected cells and non-infected antigen-presenting cells (e.g., dendritic cells) via a reaction similar to that by which the virus enters uninfected cells. Rather than destroying infected cells, as might be expected for a cellular immune response, such fusion events typically lead to the formation of short-lived multinucleated syncytial "giant cells," which actually facilitate viral replication. In this regard, while latently-infected monocytes and T-lymphocytes normally are quiescent and have no active NFκB, other cells (e.g., dendritic cells) normally contain high levels of active NFκB. However, dendritic cells do not produce SP1, while T-cells and monocytes express Sp1 in active form. Formation of syncytia between infected T-cells and dendritic cells, thus, brings active-NFκB and SP 1 into the same cell, facilitating transcription of the HIV genome.

The viral life cycle ends when mature HIV is "budded" from the host cell, retaining some amount of cell membrane as part of its envelope. Oftentimes, these budding events are localized to areas of the cell membrane where intracellular adhesion molecules (ICAMs) and other surface receptors coalesce during the cell's activation process. Because such proteins localize to regions of intercellular contact, this phenomenon (known as polar capping or polarization) can help spread the viral infection by "focusing" viral budding to an adjacent cell or in facilitating syncytia formation. Moreover, liberated virions often contain some membrane-bound ICAMs (e.g., ICAM-1), and such viruses can bind to cells (e.g., peripheral blood mononuclear cells) through interactions not involving the gp120-CD4 interaction. Such ICAM-$1^+$ HIV viruses are more infective than ICAM-$1^-$ HIV, and since they are cloaked with the host animal's glycoproteins, they are much less likely to be neutralized by circulating host antibodies. HIV can augment production of cell adhesion molecules such as ICAM-1 by precipitating the phosphorylation of STAT1α, which binds to the ICAM-1 gene enhancer and promotes SP1-dependent transcription. Interestingly, inflammatory cytokines (e.g., IFNγ) also precipitate phosphorylation of STAT1α, and the gene contains consensus binding cites for some of the same transcription factors involved in HIV replication, notably NFκB.

The presence of latent pools of HIV within quiescent cells, the high mutability of HIV proteins and their relative invisibility to immune surveillance, and the ability of the virus to alter its tropism by acquiring ICAMs all permit the virus to replicate in the face of an aggressive host immune response. Over time, the virus gradually subverts and progressively destroys the very system relied on to ward off infections. This progression of viral persistence and replication is HIV disease, and is marked by dysregulation of cytokine signaling, particularly in the lymphatic system, and ultimate destruction of lymph nodes. When HIV disease has progressed to the point where the host's immune system becomes so incapacitated that it is unable to ward off opportunistic diseases (e.g., bacteria, fungi, neoplasms, etc.), AIDS develops. Many patients begin to develop AIDS symptoms when their CD4+ T-cell count drops to about 200 (most healthy adults have a CD4+T-cell count of about 1000.

To prevent the development of AIDS, many current therapies focus on halting viral life cycle events, typically by directly targeting viral proteins. For example, gp120 antibodies have been produced in an attempt to block initial cell infection. However, due in part to the ability of the virus to spread by syncytia or direct cell-to-cell contact and its ability to acquire ICAM molecules, such attempts have met with mixed results. Other therapies employ inhibitors of HIV protease to block the formation of mature rep and cap from the rep-cap preprotein. Still other regimens employ combinations of antiviral compounds, aimed at inhibiting or attenuating viral enzymes. It has been estimated, however, that spontaneous mutations arise in HIV genes once in about $10^4$ replications (Perelson et al., *Science,* 271, 1582-86 (1996)). Given that the virus typically undergoes about $10^{10}$ replications each day, resistance to agents acting directly against viral proteins is not uncommon. Moreover, many regimens require a patient to adhere to very a strict dosing schedule involving scores of pills each day. Failure of patients to comply with such regimens adds to the failure rate of antiviral therapy. In light of these problems, there is a need for new methods, compounds, and compositions for attenuating the progression of HIV disease and other immune dysfunctions.

Many thousands of people are diagnosed with cancer and other neoplastic disorders each year, and although advances have been made in cancer therapy, the existing treatments are not successful in many cases. For example, many anticancer drugs administered to patients often have toxic effects on non-cancerous cells in the patient's body. Moreover, many neoplastic cells whose growth can be inhibited by certain drugs sometimes become resistant to those drugs. Of course, responsive tumors represent only a small fraction of the various types of neoplastic disease and, notably, there are relatively few drugs highly active against solid tumors such as ovarian cancer, breast cancer, lung cancer and the like. Thus, patients with many types of malignancies remain at significant risk for relapse and mortality. As such, there exists a continuing need for agents that inhibit neoplastic growth, especially solid tumor growth.

BRIEF SUMMARY OF THE INVENTION

The present invention provides a method, compounds, and compositions for treating a disease associated with immune dysfunction. In accordance with the method, a pharmacologically-acceptable composition including at least one resorcinol derivative compound selected from the group of compounds consisting of resorcinols, cannabinol derivatives, cannabidiol derivatives, cannabigerol derivatives, cannabichromene derivatives, and combinations thereof is administered to a patient under conditions sufficient to attenuate the dysfunction within the immune system. The invention also provides an antiviral cannabinol derivative that can be used in the inventive method. The invention also provides a (preferably alkylated) resorcinol derivative and a method of using the resorcinol derivative to attenuate the growth of a neoplasm. The method and compound are useful for treating diseases of the immune system, such as HIV disease and neoplastic disorders. These and other advantages of the present invention, as well as additional inventive features, will be apparent from the following detailed description.

DETAILED DESCRIPTION OF THE INVENTION

In one aspect, the invention provides a method for treating a disease associated with immune dysfunction. In accordance with the method, a pharmacologically-acceptable composition including at least one compound selected from the group of compounds consisting of resorcinol derivatives, cannabinol derivatives, cannabidiol derivatives, cannabigerol derivatives, and combinations thereof is administered to a patient under conditions sufficient to attenuate the dysfunction within the immune system.

The inventive method is particularly effective in combating HIV disease in humans, SIV disease in non-human primates, or FIV in feline animals. Without being bound by any particular theory, it is believed that the inventive method promotes quiescence of both actively- and latently-infected T-cells, monocytes, and macrophages, potentially through a variety of complementing mechanisms. The combination of these effects can attenuate the ability of HIV to replicate in a host immune system. Absent replication, uninfected components of the immune system are better able to clear latently-infected cells from the patient, and fewer mutation events occur. Additionally, by attenuating HIV replication, the method can reduce the probability of interpersonal transmission, (e.g., perinatal or sexual transmission). Indeed, applications of the inventive method in which the composition is administered to mucosal tissue (e.g., vaginal or rectal tissue), can retard the uptake of the virus through such tissues, thus reducing the incidence of primary infection. Thus, the invention provides a method of preventing the transmission of HIV. Furthermore, the method can guard against secondary conditions often attending HIV infection, such as destruction of lymphatic structure, CNS disease, opportunistic diseases, neoplasms, and the AIDS Wasting Syndrome.

Treatment of HIV disease can be assessed by monitoring the attenuation of its symptoms in response to the continued application of the inventive method. For example, while most healthy adult humans have a CD4+T-cell count from between about 800 to about 1200, that of HIV+ patients steadily declines, as discussed above. Therefore, the inventive method pertains to increasing, or attenuating the decrease of, the number of CD4+T-cells (typically by assaying for the CD4+/CD8+ratio) within an HIV+ patient. For example, through periodic measurements, the rate at which a given patient's CD4+T-cells is declining can be assessed both before and after commencement of therapy in accordance with the inventive method. Favorable application of the method at least slows this rate of decrease, and preferably potentiates actual gain in CD4+cell number. Similarly, the method can decrease, or attenuate the increase of, viral load (i.e., the titer of circulating HIV) within a patient. Favorable response to the treatment can also be monitored by measuring leukocyte adhesion, lymphocyte trafficking, and monocyte/macrophage mobility (i.e., a chemotaxis assay).

In one embodiment, at least one compound within the pharmacologically-acceptable composition can be a resorcinol derivative (e.g., a 5-alkyl or 3-alkyl or -acyl resorcinol). Such compounds are advantageous for use in the inventive method as they generally exhibit low cytoxicity (see, e.g., U.S. Pat. No. 5,859,067). Exemplary resorcinols can have the following formula:

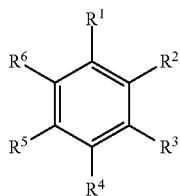

Formula I wherein,
—COR¹, —COR³, and/or —COR⁶, respectively, and preferably R³ is —COR³, and wherein R can otherwise be as follows:

$R^1$ is:
  a) H,
  b) a $C_{1-4}$ alkyl group or ester thereof,
  c) COOH,
  d) OH,
  e) a O—$C_{1-5}$ alkyl (preferably $OCH_3$) or alkanoyl, optionally substituted by mono- or dimethylamino or ethylamino groups,
  f) a O—CO—$C_{3-10}$ alkyl group containing a carboxyl or amino group,
  g)

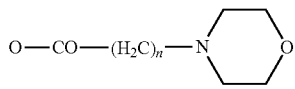

wherein n=1 to 8
  h) a p-aminobenzyl group or a $C_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative;
  i) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen (e.g., fluorine, bromine, iodine);
  j) COCOH; or
  k) $CH(CH_3)CO_2H$ or —$OCOCH_3$ $R^2$ is:
  a) H, OH, COOH, or a halogen
  b) $C_{1-6}$, carboxy or alkoxy group, or
  c) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen.

$R^3$ is:
  a) $(W)_m$—Y—$(Z)_n$, wherein
    W is a $C_{5-12}$ straight or branched (preferably 1S'$CH_3$, 2R'$CH_3$ dimethyl)alkyl (e.g., -pentyl, -hexyl, -heptyl, -octyl, or -nonyl), alkenyl, alkynyl, group, or mixture thereof, option-ally substituted with at least one halogen (e.g., halogen terminal group or even dihalogen),
    Y is a bond, O, S, SO, $SO_2$, N($C_{1-6}$ alkyl), or NCS,
    Z is:
      i) a $C_{5-12}$ alkyl, alkenyl, alkynyl, group, or mixture thereof, optionally substituted with at least one halogen, optionally substituted with a terminal aromatic ring,
      ii) $CN_{1-3}$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or
      iii) a phenyl or benzyl group, option-ally substituted with halo, $C_{1-6}$ alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, and wherein m and n are the same or different, and each is either 0 or 1,
  b) a $C_{5-12}$ alkyl or haloalkyl group, optionally substituted with a terminal aromatic ring, $CN_{1-3}NCS$, $CO_2H$, or $CO_2C_{1-4}$ alkyl, $CONH_2$, $CONHC_{1-4}$alkyl, or $CON(C_{1-4}$ alkyl$)_2$, wherein each $C_{1-4}$ alkyl on the amide nitrogen can be the same or different, or
  c) a $C_{5-12}$ alkene or alkyne group, option-ally substituted with a halogen, dithiolene, terminal aromatic ring, $CN_{1-3}$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different;

$R^4$ is:
  a) H or halogen (preferably bromine)
  b) OH, or
  c) $C_{1-6}$ alkoxyl or carboxyl;

$R^5$ is:
  a) H,
  b) a $C_{1-4}$ alkyl group,
  c) COOH,
  d) OH, or $OCH_3$,
  e) a O—$C_{1-5}$ alkyl (ether) or alkanoyl, optionally substituted with at least one mono- or di-methylamino or ethylamino group, or
  f) a lactone; and $R^6$ is:
  a) H or OH;
  b) $C_{1-4}$ alkyl (preferably ethyl), alkenyl, alkynyl, group, or mixture thereof,
  c) O—$C_{1-4}$ alkyl, alkenyl, alkynyl, group, or mixture thereof, or
  d) a prenyl, geranyl or farnesyl group, optionally substituted at any position with one or more halogens,
  e) $(W)_m$—Y—$(Z)_n$, wherein
    W is a $C_{5-12}$ alkyl, alkenyl, alkynyl, group, or mixture thereof, optionally substituted with at least one halogen,
    Y is a bond, O, S, SO, $SO_2$, CO, NH, N($C_{1-4}$ alkyl), or NCS,
    Z is:
      i) a $C_{5-12}$ alkyl, alkenyl, alkynyl, group, or mixture thereof, optionally substituted with at least one halogen, optionally substituted with a terminal aromatic ring,
      ii) $CN_{1-3}$, $CO_2H$, or $CO_2C_{1-4}$ alkyl, $CONH_2$, $CONHC_{1-4}$alkyl, or $CON(C_{1-4}$ alkyl$)_2$, wherein each $C_{1-4}$ alkyl on the amide nitrogen can be the same or different, or
      iii) a phenyl or benzyl group, optionally substituted with halo, $C_{1-6}$, alkyl, $C_{1-6}$ alkoxy, $C_{1-6}$ alkylthio, CN, $CF_3$, CO, H, or $CO_2C_{1-4}$ alkyl, $CONH_2$, $CONHC_{1-4}$ alkyl, or $CON(C_{1-4}$alkyl$)_2$, wherein each $C_{1-4}$ alkyl on the amide nitrogen can be the same or different, and wherein m and n are the same or different, and each is either 0 or 1,
f) a $C_{5-12}$ alkyl or haloalkyl group, optionally substituted with a terminal aromatic ring, CN, $CH_2N_3$, NCS, $CO_2H$, or $CO_2C_{1-4}$ alkyl, $CONH_2$, $CONHC_{1-4}$alkyl, or $CON(C_{1-4}$ alkyl$)_2$, wherein each $C_{1-4}$ alkyl on the amide nitrogen can be the same or different,
g) a $C_{5-12}$ alkene or alkyne group, optionally substituted with a halogen, dithiolene, terminal aromatic ring, CN, $CH_2N_3$, NCS, $CO_2H$, or $CO_2C_{1-4}$ alkyl, $CONH_2$, $CONHCl$ alkyl, or $CON(C_{1-4}$ alkyl$)_2$, wherein each $C_{1-4}$ alkyl on the amide nitrogen can be the same or different, or
h) $CH(CH_3)$ CO2H, $CH_2OOOH$, or $—OCOCH_3$.

Compounds according to Formula I preferably include a lactone, H, OH or $OCH_3$, $—CH(CH_3)CO_2H$, or $—OCOCH_3$ as $R^1$ substituents. Preferred substituents at $R^2$ are hydrogen, halogen (most preferably fluorine) hydroxyl, COON, or methoxyl groups. Preferred substituents at $R^4$ include H or a halogen (most preferably bromine). Preferred substituents at $R^5$ include a lactone, H, OH, and $OCH_3$. Preferred substituents at $R^6$ include H, OH, ethyl, $CH(CH_3)CO_2H$, $CH_2COOH$, and $—OCOCH_3$. Where compounds of formula I are included, preferably $R^6$ is methyl or ethyl. A more preferred compound according to Formula I has hydroxyl substituents at $R^1$, $R^5$, and a methyl substituent at $R^6$; even more preferably, the compound has a third hydroxyl substituent at $R^2$. Preferred substituents at $R^3$ are discussed elsewhere herein; however, the invention provides compounds according to Formula I, wherein $R^3$ is:
a) $(W)_m—Y—(Z)_n$, wherein
W is a $C_{5-12}$ alkyl, alkenyl, alkynyl (e.g., 2'-ynyl, 3'-ynyl or 4'-ynyl), group, or mixture thereof, optionally substituted with at least one halogen,
Y is a bond, O, S, SO, $SO_2$, CO, NH, $N(C_{1-6}$ alkyl), or NCS,
Z is:
i) a $C_{5-12}$ alkyl, alkenyl, alkynyl (e.g., 2'-ynyl, 3'-ynyl or 4'-ynyl), group, or mixture thereof, optionally substituted with at least one halogen, optionally substituted with a terminal aromatic ring,
ii) $CN_{1-3}$, $CO_2H$, or $CO_2C_{1-4}$ alkyl, $CONH_2$, $CONHC_{1-4}$ alkyl, or $CON$ $(C_{1-4}$alkyl$)_2$, wherein each $C_{1-4}$ alkyl on the amide nitrogen can be the same or different, or
iii) a phenyl or benzyl group, optionally substituted with halo, $C_{1-6}$ alkyl, $C_{1-6}$ alkoxy, C alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different,
wherein at least one of W and Z includes a branched chain and
wherein m and n are the same or different, and each is either 0 or 1,
b) a terminally-branched, e.g., terminal dimethyl, $C_{5-12}$ alkyl or haloalkyl group, optionally substituted with a terminal aromatic ring, CN, $CH_2N_3$, NCS, $CO_2H$, or $CO_2C_{1-4}$alkyl, $CONH_2$, $CONHC_{1-4}$ alkyl, or $CON(C_{1-4}$ alkyl$)_2$, wherein each $C_{1-4}$alkyl on the amide nitrogen can be the same or different, or
c) a terminally-branched $C_{5-12}$ alkene or alkyne group, optionally substituted with a halogen, dithiolane, terminal aromatic ring, CN, $CH_2N_3$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different.

Particularly preferred $R^3$ substituents include $C_5$-$C_{12}$ alkynes, and particularly preferred groups also include di- or tri-methyl terminal groups. A most preferred substituent at $R^3$ is a dimethylheptyl, particularly 1'S, 2'SR, and also preferably with terminal halogen (or dihalogen) substituents, and another preferred substituent is 5,5-dimethyl Hex(1-en-3-ynyl) e.g., compound Ii). Many such compounds exhibit antineoplastic activity and can be employed as such, as described herein. While any such compounds can be included within the composition in accordance with the inventive method, some preferred compounds are as follows:

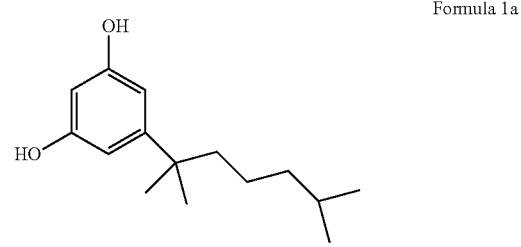

Formula Ia

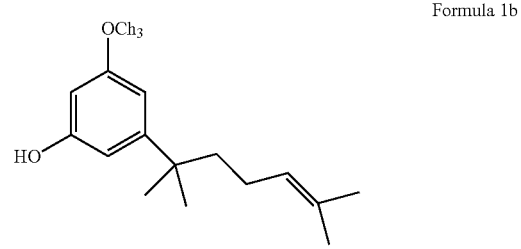

Formula Ib

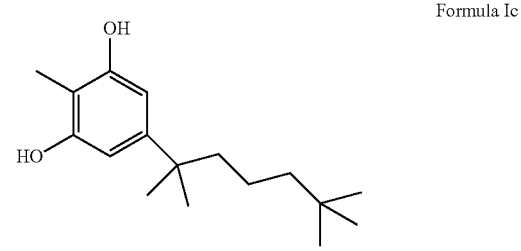

Formula Ic

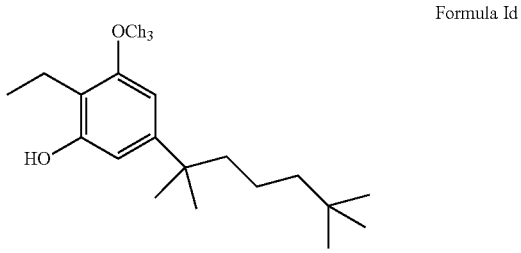

Formula Id

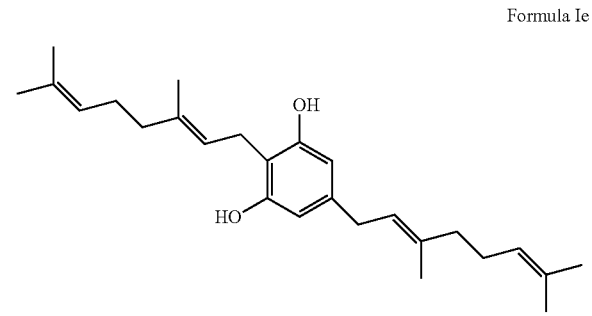

Formula Ie

-continued

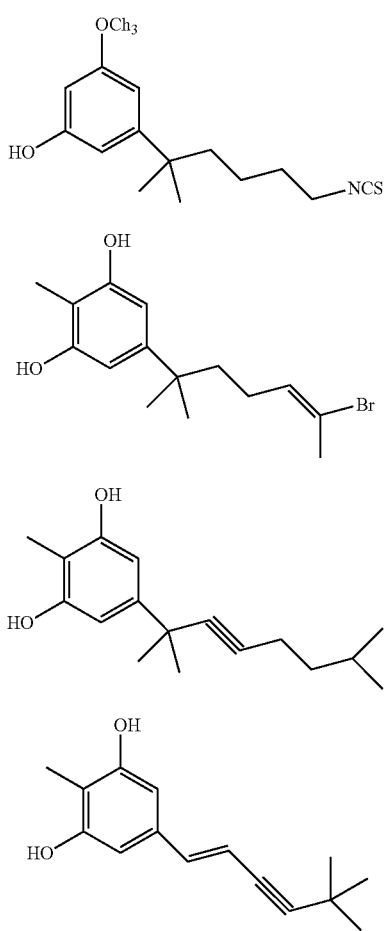

Formula If

Formula Ig

Formula Ih

Formula Ii

As mentioned, compounds according to Formula I can have geranyl substituents at $R^6$. In this regard, at least one compound within the pharmacologically-acceptable composition can be cannabigerol or a derivative thereof having the following formula:

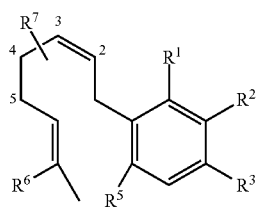

Formula II wherein:

$R^1$ is:
a) H,
b) a $C_{1-4}$ alkyl group or ester thereof,
c) COOH,
d) OH,
e) a O—$C_{1-5}$ alkyl (preferably $OCH_3$) or alkanoyl, optionally substituted by mono- or dimethylamino or ethylamino groups,
f) a O—CO—$C_{3-10}$ alkyl group containing a carboxyl or amino group,
g)

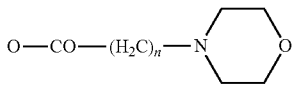

wherein n=1 to 8 h) a p-aminobenzyl group or a $C_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative;
i) $R^1$ and $R^2$ comprise a substituent of the formula —$O(CH_2)_{2-5}$, wherein $R^1$ and $R^2$,
together with the carbon atoms to which they are bonded, comprises a ring where at least one hydrogen atom thereof is optionally substituted with a halogen (e.g., fluorine, chlorine, bromine, iodine);
j) COCOH; or
k) $CH(CH_3)CO_2H$ or —$OCOCH_3$ $R^2$ is:
a) H, OH, COOH, or a halogen
b) $C_{1-6}$, carboxy or alkoxy group, or
c) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen.

$R^3$ is:
a) $(W)_m$—Y—$(Z)_n$, wherein
W is a $C_{5-12}$ straight or branched (preferably 1S'CH3, 2R'CH3 dimethyl) alkyl, alkenyl, alkynyl, group, or mixture thereof, optionally substituted with at least one halogen,
Y is a bond, O, S, SO, $SO_2$, CO, NH, N($C_{1-6}$ alkyl), or NCS,
Z is:
i) a $C_{5-12}$ alkyl, alkenyl, alkynyl, group, or mixture thereof, optionally substituted with at least one halogen, optionally substituted with a terminal aromatic ring,
ii) CN, CH2N3, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or
iii) a phenyl or benzyl group, optionally substituted with halo, $C_{1-6}$ alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, and
wherein
m and n are the same or different, and each is either 0 or 1,
b) a $C_{5-12}$ alkyl or haloalkyl group, optionally substituted with a terminal aromatic ring, CN, $CH_2N_3$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or
c) a $C_{5-12}$ alkene or alkyne group, optionally substituted with a halogen, dithiolane, terminal aromatic ring, CN, $CH_2N_3$, NCS, $CO_2H$, or $CO_2C_{1-4}$ alkyl, $CONH_2$, CONHC$_{1-4}$ alkyl, or CON(C$_{1-4}$ alkyl)$_2$, wherein each C$_{1-4}$ alkyl on the amide nitrogen can be the same or different;

R$^5$ is:
a) H,
b) a C$_{1-4}$ alkyl group,
c) COOH,
d) OH, or OCH$_3$,
e) a O—C$_{1-5}$ alkyl (ether) or alkanoyl, optionally substituted with at least one mono- or di-methylamino or ethylamino group, or
f) a lactone; and R$^6$ is:
a) hydrogen,
b) C$_{1-6}$ alkoxy, C$_{1-6}$ alkylthio, C$_{1-6}$ alkyl (preferably ethyl), or C$_{1-6}$ haloalkyl,
c) CN,
d) CO$_2$H,
e) CO$_2$—C$_{1-4}$ alkyl,
f) C(Y)(Z)—OH,
g) C(Y)(Z)—O—C$_{1-4}$ alkyl, or C$_{1-6}$ alkyl-CO$_2$—Y
wherein Y and Z are each independently H or C$_{1-4}$ alkyl, R$^7$ is:
a) hydroxy (preferably (3-hydroxy) or lactone,
b) halo,
c) C$_{1-6}$ alkoxy, C$_{1-6}$ alkylthio, C$_{1-6}$ alkyl, or C$_{1-6}$ haloalkyl,
d) CN,
e) N$_3$,
f) CO$_2$H,
g) CO$_2$C$_{1-4}$ alkyl,
h) C(Y)(Z)—OH,
i) C(Y)(Z)—O—C$_{1-4}$ alkyl,
j) C$_{1-6}$ alkyl-CO$_2$—Y, or
k) =O or =S,
wherein Y and Z are each independently H or C$_{1-6}$ alkyl, and wherein R$^7$ can be at any of positions 2-5.

Compounds according to Formulas I and II can be synthesized using known procedures from commercially available starting materials (see, e.g., Dominianni et al., J. Org. Chem., 42, 344-46 (1977); Back et al., Arch. Pharm. Res., 19, 228-30 (1996); Guthrie et al., J. Org. Chem. 47, 2369-76 (1982)). For example, acid catalyzed condensation of 2,6-dimethoxyphenol with OH—R$^3$ can produce a 4-alkylphenol intermediate. Conversion of the phenolic group to the diethylphosphate ester followed by reduction with lithium metal in liquid ammonia can then produce a dimethoxybenzene derivative. Mono- or didemethylation of this compound (e.g., with boron tribromide) can then yield the desired methoxyphenol and/or resorcinol (Formula I), respectively. Compounds of Formula I having alkyl substituents at R$^6$ can be prepared, for example, first by lithiation of the dimethoxybenzene derivative at R$^6$ (e.g., in the presence of Bu/THF) and subsequent exposure to an alkylating agent (e.g., methyl or ethyl iodide or sulfate). Mono- or didemethylation of this compound (e.g., with boron tribromide) can then yield the desired methoxyphenol and/or resorcinol (Formula I), respectively, having the alkyl substituents at R$^6$. Compounds of Formula II can be prepared, for example, by acid catalyzed condensation of a methoxyphenol and/or resorcinol (Formula I) having a desired substituents at R$^3$ with geraniol (e.g., in the presence of BF$_3$, Et$_2$O, silica, and CH$_2$Cl$_2$). Of course, these compounds can be synthesized by other appropriate methods, many of which are known in the art.

In another embodiment at least one compound within the pharmacologically acceptable composition is a cannabinol derivative having the following formula:

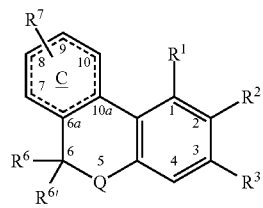

Formula III wherein,
R$^1$ is:
a) H,
b) a C$_{1-4}$ alkyl group or ester thereof,
c) COOH,
d) OH,
e) a O—C$_{1-5}$ alkyl (preferably OCH$_3$) or alkanoyl, optionally substituted by mono- or dimethylamino or ethylamino groups,
f) a O—CO—C$_{3-10}$ alkyl group containing a carboxyl or amino group,
g)

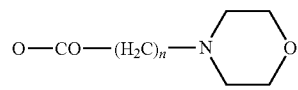

wherein n=1 to 8
h) a p-aminobenzyl group or a C$_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof and an activated derivative of the carboxyl terminated derivative;
i) R$^1$ and R$^2$ comprise a substituent of the formula —O(CH$_2$)$_{3-5}$, wherein R$^1$ and R$^2$, together with the carbon atoms to which they are bonded, comprises a ring where at least one hydrogen atom thereof is optionally substituted with a halogen;
j) COCOH; or
k) CH(CH$_3$)CO$_2$H or —OCOCH$_3$ R$^2$ is:
a) H, OH, COOH, or a halogen
b) C$_{1-6}$ carboxy or alkoxy group, or
c) R$^1$ and R$^2$ comprise a substituent of the formula —O(CH$_2$)$_{3-5}$, wherein R$^1$ and R$^2$, together with the carbon atoms to which they are bonded, comprises a ring where at least one hydrogen atom thereof is optionally substituted with a halogen R$^3$ is:
a) (W)$_m$—Y—(Z)$_n$, wherein
W is a C$_{5-12}$ straight or branched (preferably 1S'CH$_3$, 2R'CH$_3$ dimethyl) alkyl, alkenyl, alkynyl, group, or mixture thereof, optionally substituted with at least one halogen,
Y is a bond, O, S, SO, SO$_2$, CO, NH, N(C$_{1-6}$ alkyl) or NCS,
Z is:
i) a C$_{5-12}$ alkyl, alkenyl, alkynyl groups, or mixture thereof, optionally substituted with at least one halogen, optionally substituted with a terminal aromatic ring, ii) $CN_{1-3}$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or iii) a phenyl or benzyl group, optionally substituted with halo, $C_{1-6}$ alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, and wherein m and n are the same or different, and each is either 0 or 1, b) a $C_{5-12}$ alkyl or haloalkyl group, optionally substituted with a terminal aromatic ring, CN, $CH_2N_3$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or c) a $C_{5-12}$ alkene or alkyne group, optionally substituted with a halogen, dithiolene, terminal aromatic ring, CN, $CH_2N_3$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different;

$R^6$ and $R^{6'}$ together form =O or =S, or each is independently selected from the group consisting of:
a) hydrogen,
b) $C_{1-6}$ alkoxy, $C_{1-6}$ alkylthio, $C_{1-6}$ alkyl, or $C_{1-6}$ haloalkyl,
c) CN,
d) $CO_2H$,
e) $CO_2$—$C_{1-4}$ alkyl,
f) C(Y) (Z)—OH,
g) C(Y) (Z)—O—$C_{1-4}$ alkyl, and
h) $C_{1-6}$ alkyl-$CO_2Y$,
wherein Y and Z are each independently H or $C_{1-6}$ alkyl, $R^7$ is
a) hydroxy or lactone,
b) halo,
c) $C_{1-6}$ alkoxy, $C_{1-6}$ alkylthio, $C_{1-6}$ alkyl, or $C_{1-6}$ haloalkyl,
d) CN,
e) $N_3$,
f) $CO_2H$,
g) $CO_2$—$C_{1-4}$ alkyl,
h) C(Y) (Z)—OH,
i) C(Y) (Z)—$C_{1-4}$ alkyl,
j) $C_{1-6}$ alky-$CO_2$—Y, or
k) =O or =S,
wherein Y and Z are each independently H or $C_{1-6}$ alkyl;

Q is:
a) O or S, or
b) N—W,
wherein W is:
i) hydrogen,
ii) $C_{1-6}$ alkoxyalkyl, $C_{1-6}$ alkyl, or $C_{1-6}$ haloalkyl
iii) $OC_{1-6}$ alkyl, or $OC_{1-6}$ haloalkyl,
iv) CN,
v) $C_{1-6}$ alkyl,
vi) C(Y) (Z) $Cl_{-4}$ alkyl, or
vii) $C_{1-6}$ alkyl-$CO_2$—Z,
wherein Y and Z are each independently H or $C_{1-6}$ alkyl.

It is known in the art that some compounds according to Formula III are psychoactive, chiefly via agonism of the CB1 receptor. Thus, in some applications, it may be preferable to employ substituents within Formula III (e.g., of $R^1$-$R^7$, Q, and ring C) that preferably promote CB2 agonist activity, rather than CB1 activity, and are more preferably substituents that promote selective CB2 agonist activity. In some embodiments, to mitigate or eliminate psychoactive effects attributed to some cannabinoids, the inventive method employs a selective CB2 agonist, which is one that preferentially acts on the CB2 receptor, as opposed to the CB1 receptor. Most preferably, the selective CB2 agonist does not bind the CB1 receptor at concentrations in which it activates the CB2 receptor. Various selective CB2 agonists are known in the art. Examples of such compounds include classical and nonclassical cannabinoids, bicyclic cannabinoids, aminoalkylindoles, and eicosanoids (see, e.g., Pertwee, *Pharmacol. Ther,* 74(2), 129-80 (1997)). To assess whether a given compound is a selective CB2 agonist, its relative affinity for the CB2 and CB 1 receptors can be assessed using any suitable method, for example using cells engineered to express the receptors (Ross et al., *Br J. Pharmacol.,* 126, 665-72 (1999)). Such values typically are expressed as a binding constant, K, from which a ratio of $K_i/K_{i\_32}$ can be calculated. Desirably, the selective CB2 agonist has a $K_i$ for the CB2 receptor of from about 100 nM to about 0.1 nM, preferably from about 25 nM to about 0.2 nM, such as from about 15 nM to about 0.5 nM. Moreover, the ratio of $K_{i--CB1}/K_{i-CB2}$ is at least about 1.5, and more preferably at least about 5 (e.g., at least about 10). Many compounds are known to have suitable CB2 selectivity for use as a CB2 agonist in the inventive method. For example, JWH-015 has a $K_{i-CB2}$ of 13.8±4.6 nM and a $K_{i-CB1}$ $K_{i-CB2}$ ratio of 27.5; WIN-55, 212-2 has a $K_{i-CB2}$ of 0.028±0.16 nM and a $K_{i-CB1}/K_{i-CB2}$ ratio of 6.75; 5-F4B-THO has a $K_{i-CB2}$ of 8.7.±3.5 nM and a $K_{i-CB1}/K-_{CB2}$ ratio of 6.55; JWH-018 has a $K_{i-CB2}$ of 2.94±2.65 nM and a $K_{i-CB1}/K_{i-CB2}$ ratio of 3.23; CP-56,667 has a $K_{i-CB2}$ of 23.6±6.5 nM and a $K_{i-CB1}/K_{i-CB2}$ ratio of 2.61; L759656 has a $K_{i-CB2}$ of 11.8±2.5 nM and a $K_{i-CB1}/K_{i-CB2}$ ratio of 414.24; and L759633 has a K of 6.4±2.2 nM and a $K_{i-CB1}/K_{i-CB2}$ ratio of 162.97 (see above-referenced references). It is within the ordinary skill in the art to assess these values for yet-unmeasured (or novel) compounds. Aside from binding the CB2 receptor preferentially, a preferred selective CB2 agonist exhibits greater CB2-directed physiological response than CBI response. A classic assay for differential activity measures the ability of a compound to inhibit drug-induced cyclic AMP (cAMP) production in cells engineered to express the respective receptor, typically expressed as $EC_{50}$ (a percent-age of maximal effects) (Ross et al., *Br J, Pharmacol.,* 126, 665-72 (1999)). Preferably, selective CB2 agonist typically exhibits a $EC_{50-CB2}/EC_{50-CB1}$ ratio of greater than about 10, more typically greater than about 100 (e.g., greater than about 500). Many compounds are known to have suitable CB2 selectivity, and thus can be used as a CB2 agonist in the inventive method. For example, L759656 has an $EC_{50CB2}/EC_{50CB1}$ ratio of >3000; and L759633 has a $EC_{50CB2}/EC_{50CB1}$ ratio of >1000. It is within the ordinary skill in the art to assess these values for yet-unmeasured (or novel) compounds.

For CB2 selectivity, $R^1$ in Formula III preferably is not OH, as it is in the natural cannabinol and tetrahydrocannabinol compounds. Rather, preferably $R^1$ in Formula III is H, O—$C_{1-4}$alkyl (more preferably methoxy) or a hemi ester of succinic acid, malonic acid or the alaninate ester of alanine and salts thereof. In another preferred embodiment, $R^1$ and $R^2$ together comprise a substituent of the formula —$O(CH_2)_{3-5}$, wherein $R^1$ and $R^2$, together with the carbon atoms to which they are bonded, comprise a ring where at least one hydrogen atom thereof is optionally substituted with a halogen (e.g., an 0,2 propano ring). Furthermore, where $R^2$Formula III is a halogen, preferably it is iodo. Preferably, $R^6$ and $R^{6'}$ together form =O or each are methyl, ethyl, or methoxy. While $R^7$ can be at any of positions 7-10 of ring C, preferably it is at position 9 of the ring. Where it is desired to promote CB2 selectivity, $R^7$ preferably is electronegative (e.g., COOH, halogen, 13-hydroxy, or lactone.), and to enhance activity, it can be substituted with either a lactone or a hydroxy group.

Ring C in Formula III can be any of the following (the dashed lines representing a double bond at Δ6a-10a, Δ8-9, or Δ9-10 position):

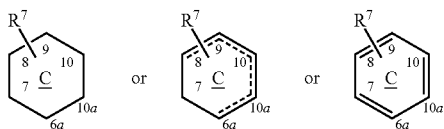

However, to promote CB2 selectivity, preferably the ring is aromatic. In this regard, a preferred embodiment of the invention provides novel anti-viral cannabinol derivatives according to Formula III, wherein ring C is aromatic. In such compounds, $R^7$ preferably is electronegative and more preferably is on C9. Furthermore, $R^1$ preferably is other than OH and preferably is deoxy, an ester, or ether. Exemplary cannabinol derivative compounds include:

Formula IIIa
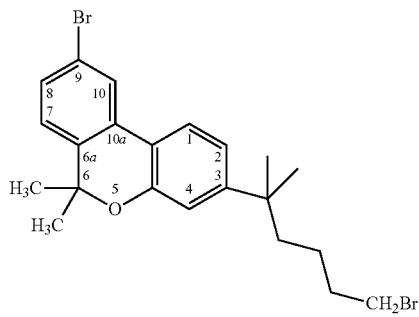

Formula IIIb
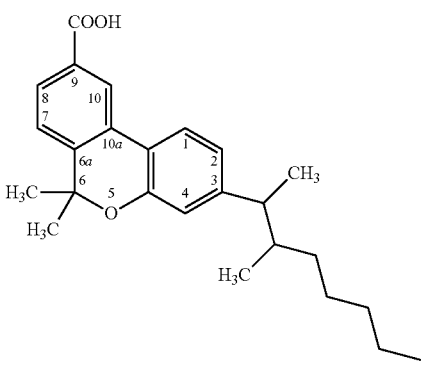

-continued

Formula IIIc
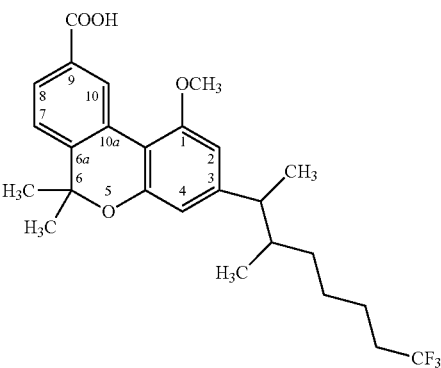

Formula IIId
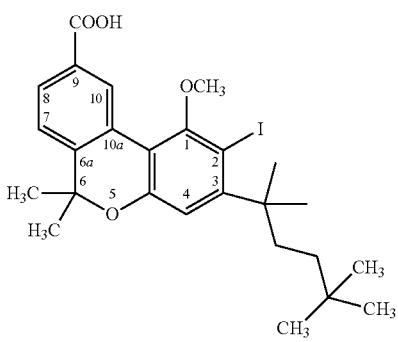

Formula IIIe
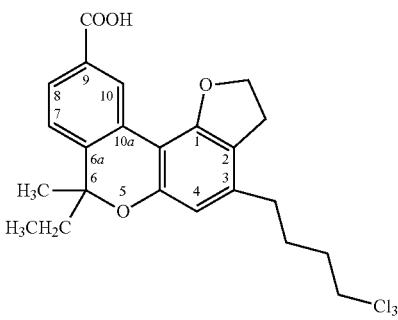

Formula IIIf
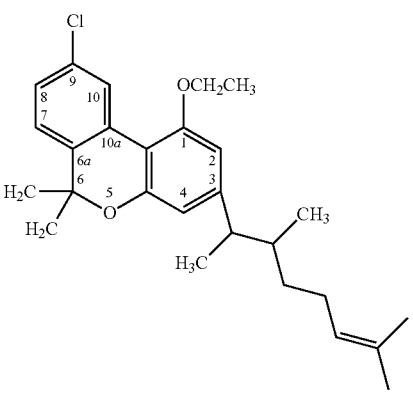

Many compounds according to Formula III are well known, and others can be manufactured in accordance with published methods (see, for example, International Patent Application WO99/20268 (Burstein), and U.S. Pat. No. 2,509,386 (Adams), U.S. Pat. No. 3,799,946 (Loev), U.S. Pat. No. 3,856,821 (Loev), U.S. Pat. No. 3,897,306 (Vidic et al.), U.S. Pat. No. 4,064,009 (Fukada et al.), U.S. Pat. No. 4,087, 545 (Archer et al.), U.S. Pat. No. 4,142,139 (Bindra), U.S.

Pat. No. 4,309,545 (Johnson), U.S. Pat. No. 4,599,327 (Nogradi et al.), U.S. Pat. No. 4,833,073 (McNally et al.), U.S. Pat. No. 4,876,276 (Mechoulan et al.), U.S. Pat. No. 4,973,603 (Burstein), U.S. Pat. No. 5,338,753 (Burstein et al.), U.S. Pat. No. 5,389,375 (ElSohly), U.S. Pat. No. 5,440,052 (Makriyannis et al.), U.S. Pat. No. 5,605,906 (Lau), and U.S. Pat. No. 5,635,530 (Mechoulam et al.); and Charalambous et al., *Pharm. Biochem. Behav.*, 40, 509-12 (191), Gareau et al., *Bioorg. Med. Chem. Lett.*, 6(2), 189-94 (1996), Griffin et al., *Br J. Pharmacol.*, 126, 1575-84 (1999), Huffman et al., *Bioorg. Med. Chem. Lett.*, 6, 2281-88 (1998), Lemberger et al., *Clin. Pharmacol. Ther*, 18(6), 720-26 (1975), Loev et al., *J. Med. Chem.*, 16(11), 1200-06 9 (1973), Loev et al., *J. Med. Chem.*, 17(11), 1234-35 (1974), Martin et al., *Pharm. Biochem. Behav.*, 46, 295-301 (1993), Papahatjis et al., *J. Med. Chem.*, 411(7), 1195-1200 (1998), Pars et al., *J. Med. Chem.*, 19(4), 445-53 (1976), Pertwee et al., *Pharmacol. Ther*, 74(2), 129-80 (1997), Razdan et al., *J. Med. Chem.*, 19(4), 454-60 (1976), Razdan, *Pharmacol. Reviews*, 38(2) 75-149 (1980), Reggio et al., *J. Med. Chem.*, 40(20), 3312-18 (1997), Reggio et al., *Life Sci.*, 56(23/24), 2025-32 (1995), (Ross et al., *Br J. Pharmacol.*, 126, 665-72 (1999), Thomas et al., *J. Pharm. Exp. Ther*, 285(1), 285-92 (1998), Wiley et al., *J. Pharm. Exp. Ther*, 285(1), 995-1004 (1998), Winn et al., *J. Med. Chem.*, 19(4), 461-71 (1976), and Xie et al., *J. Med. Chem.*, 41, 167-74 (1998)).

In the preferred embodiment wherein ring C of Formula III is aromatic, such compounds additionally can be manufactured by aromatizing an appropriate tetrahydrocannabinol (THC) derivative molecule by known methods (see, e.g., Adams et al., *J. Am. Chem. Soc.*, 62, 23401 (1940); Ghosh et al., *J. Chem. Soc.*, 1393 (1940); and Adams et al., *J. Am. Chem. Soc.*, 70, 664 (1948)). For example, aromatization of such compounds can occur by heating the compound with sulfur at about 238-240° C., under a nitrogen atmosphere, for about 4 hours (Rhee et al., *J. Med. Chem.*, 40(20), 3228-33 (1997)). Other suitable methods include aromatization using a catalyst (e.g., palladium on carbon) or a chemical dehydrogenating agent (e.g., 2,3-dichloro-5,6-dicyanoquinone) (see, for example, U.S. Pat. No. 3,799,946 (Loev)).

As mentioned, in some applications of the inventive method, particularly where at least one of the compounds within the composition is a cannabinol derivative, it is desirable to mitigate potentially deleterious psychoactivity attributed to some such compounds. As an alternative to employing non-psychoactive cannabinol derivatives (e.g., selective CB2 agonists) within the composition, other pharmacologically-active agents can be employed in addition to mitigate psychoactive effects. For example, as some of the aforementioned compounds might exert some activity on CBI receptors, it is often desirable to adjunctively administer a selective CB1 antagonist to the patient. Indeed, in some applications it is desired to co-administer a non-selective CB2 agonist (e.g., Δ8- or Δ9-THC and derivatives thereof) in small doses, in which cases administration of a CB1 antagonist is preferred. Many suitable selective CBI antagonists are known in the art (Rinaldi-Carmona et al., *FEBS Lett.*, 350, 240-44 (1994), see also U.S. Pat. No. 5,624,941 (Barth et al.), U.S. Pat. No. 5,747,524 (Cullinan et al.), U.S. Pat. No. 5,925,768 (Barth et al.)). SR-1241716A is a particularly potent, and theretofore preferred, selective CBI antagonist for use in the inventive method. Other preferred selective CBI antagonists are cannabidiol and its derivatives (see, e.g., U.S. Pat. No. 2,304,669 (Adams); Razdan et al., *Pharmacol. Reviews*, 38(2), 75-149 (1986); Reggio et al., *Life Sci.*, 56(23-24), 2025-32 (1995)), as these potently antagonize the CB1 receptor. In addition to antagonizing CB1, cannabidiol and many of its derivatives also advantageously attenuate the cytochrome $P_{450}$ system in the liver, leading to enhanced bioavailability of other compounds within the composition (e.g., Bornheim et al., *Chem. Res. Toxicol.*, 11, 1209-16 (1998)). In this regard, in some embodiments of the inventive method, at least one compound within the pharmacologically-acceptable composition is cannabidiol or a derivative thereof having the following formula:

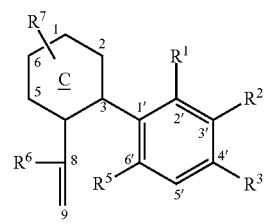

Formula IV wherein:

$R^1$ is:
a) H,
b) a $C_{1-4}$ alkyl group or ester thereof, c) COOH,
d) OH,
e) a O—$C_{1-5}$ alkyl (preferably $OCH_3$) or alkanoyl, optionally substituted by mono- or di-methylamino or ethylamino groups,
f) a O—CO—$C_{3-10}$ alkyl group containing a carboxyl or amino group,
g)

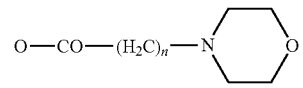

wherein n=1 to 8
h) a p-aminobenzyl group or a $C_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative;
i) $R^1$ and $R^2$ comprise a substituent of the formula —O$(CH_2)_{2-5}$, wherein $R^1$ and $R^2$, together with the carbon atoms to which they are bonded, comprises a ring where at least one hydrogen atom thereof is optionally substituted with a halogen (e.g., fluorine, chlorine, bromine, iodine);
j) COCOH; or
k) $CH(CH_3) CO_2H$ or —$OCOCH_3$
$R^2$ is:
a) H, OH, COOH, or a halogen
b) $C_{1-6}$, carboxy or alkoxy group, or
c) $R^1$ and $R^2$ comprise a substituent of the formula —O$(CH^2)_{3-5}$, wherein $R^1$ and $R^2$, together with the carbon atoms to which they are bonded, comprises a ring where at least one hydrogen atom thereof is optionally substituted with a halogen.
$R^3$ is:
a) $(W)_m$—Y—$(Z)_n$, wherein
W is a $C_{5-12}$ straight or branched (preferably 1S'$CH_3$, 2R'$CH_3$ dimethyl)alkyl, alkenyl, alkynyl, group, or mixture thereof, optionally substituted with at least one halogen,
Y is a bond, O, S, SO, $SO_2$, N($C_{1-6}$ alkyl), or NCS, Z is:
   i) a $C_{5-12}$ alkyl, alkenyl, alkynyl, group, or mixture thereof, optionally substituted with at least one halogen, optionally substituted with a terminal aromatic ring,
   ii) CN, $CH_2N_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or iii) a phenyl or benzyl group, option-ally substituted with halo, $C_{1-6}$ alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, and wherein m and n are the same or different, and each is either 0 or 1,
b) a $C_{5-12}$ alkyl or haloalkyl group, optionally substituted with a terminal aromatic ring, CN, $CH_2N_3$, NCS, $CO_2H$, or $CO_2C_{1-4}$ alkyl, $CONH_2$, $CONHC_{1-4}$alkyl, or $CON(C_{1-4}$ alkyl$)_2$, wherein each $C_{1-4}$ alkyl on the amide nitrogen can be the same or different, or
c) a $C_{5-12}$ alkene or alkyne group, option-ally substituted with a halogen, dithiolene, terminal aromatic ring, $CN_{1-3}$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different;

$R^5$ is:
a) H
b) a $C_{1-4}$ alkyl group
c) COOH
d) OH, or
e) a O—$C_{1-5}$ alkyl (ether) or alkanoyl, optionally substituted with at least one mono- or di-methylamino or ethylamino group;

$R^6$ is:
a) hydrogen,
b) $C_{1-6}$ alkoxy, $C_{1-6}$ alkylthio, $C_{1-6}$ alkyl, or $C_{1-6}$ haloalkyl
c) CN,
d) $CO_2H$,
e) $CO_2C_{1-4}$ alkyl,
f) C(Y)(Z)—OH
g) C(Y)(Z)—O—$C_{1-4}$ alkyl, or
h) $C_{1-6}$ alkyl-$CO_2$—Y,
wherein Y and Z are each independently H or $C_{1-6}$ alkyl, $R^7$ is:
a) hydroxy or lactone,
b) halo,
c) $C_{1-6}$ alkoxy, $C_{1-6}$ alkylthio, $C_{1-6}$-carboxy, or $C_{1-6}$ haloalkyl,
d) CN,
e) $N_3$,
f) $CO_2H$,
g) $CO_2$—$C_{1-4}$ alkyl,
h) C(Y)(Z)—OH,
i) C(Y)(Z)—O—$C_{1-4}$ alkyl,
j) $C_{1-6}$ alkyl-$CO_2$—Y, or
k) =O or =S,
wherein Y and Z are each independently H or $C_{1-6}$ alkyl, and wherein $R^7$ can be at any of positions 1, 2, 5, or 6 of ring C.

Another preferred compound for use in the inventive method is a cannabichromene derivative having the following formula:

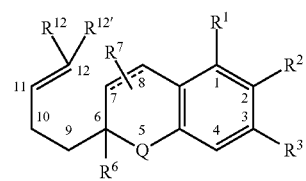

Formula V wherein,
$R^1$ is:
   a) H,
   b) a $C_{1-4}$ alkyl group or ester thereof,
   c) COOH,
   d) OH,
   e) a O—$C_{1-5}$ alkyl (preferably $OCH_3$) or alkanoyl, optionally substituted by mono- or dimethylamino or ethylamino groups,
   f) a O—CO—$C_{3-10}$ alkyl group containing a carboxyl or amino group,
   g)

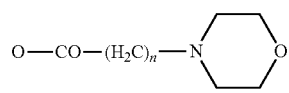

wherein n=1 to 8
   h) a p-aminobenzyl group or a $C_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative;
   i) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen (e.g., fluorine, chlorine, bromine, iodine, astatine);
   j) COCOH; or
   k) $CH(CH_3)CO_2H$ or —$OCOCH_3$ $R^2$ is:
   a) H, OH, COOH, or a halogen
   b) $C_{1-6}$ carboxy or alkoxy group, or
   c) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen.

$R^3$ is:
a) $(W)_m$—Y—$(Z)_n$, wherein
W is a $C_{5-12}$ straight or branched (preferably 1S'$CH_3$, 2R'$CH_3$ dimethyl) alkyl, alkenyl, alkynyl, group, or mixture thereof, optionally substituted with at least one halogen,
Y is a bond, O, S, SO, $SO_2$, CO, NH, N($C_{1-4}$ alkyl), or NCS,
Z is:
   i) a $C_{5-12}$ alkyl, alkenyl, alkynyl, group, or mixture thereof, optionally substituted with at least one halogen, optionally substituted with a terminal aromatic ring,
   ii) CN, $CH_2N_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or iii) a phenyl or benzyl group, optionally substituted with halo, $C_{1-6}$ alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, and wherein m and n are the same or different, and each is either 0 or 1,
b) a $C_{5-12}$ alkyl or haloalkyl group, optionally substituted with a terminal aromatic ring, CN, $CH_2N_3$, NCS, $CO_2H$, or $CO_2C_{1-4}$ alkyl, $CONH_2$, $CONHC_{1-4}$alkyl, or $CON(C_{1-4}$ alkyl$)_2$, wherein each $C_{1-4}$ alkyl on the amide nitrogen can be the same or different, or
c) a $C_{5-12}$ alkene or alkyne group, option-ally substituted with a halogen, dithiolane, terminal aromatic ring, CN, $CH_2N_3$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different;
$R^6$ is selected from the group consisting of:
a) hydrogen,
b) hydroxy or lactone,
c) halo,
d) $C_{1-6}$ alkoxy, $C_{1-6}$ alkylthio, $C_{1-6}$ alkyl, or $C_{1-6}$ haloalkyl,
e) CN,
f) $N_3$,
g) $CO_2H$,
h) $CO_2$—$C_{1-4}$ alkyl,
i) C(Y)(Z)—OH,
j) C(Y)(Z)—O—$C_{1-4}$ alkyl, and
k) $C_{1-6}$ alkyl-$CO_2$—Y,
wherein Y and Z are each independently H or $C_{1-6}$ alkyl,
$R^7$ is selected from the group consisting of:
a) hydrogen,
b) hydroxy or lactone,
c) halo,
d) $C_{1-6}$ alkoxy, $C_{1-6}$ alkylthio, $C_{1-6}$ alkyl, or $C_{1-6}$ haloalkyl,
e) CN,
f) N3,
g) $CO_2H$,
h) $CO_2$—$C_{1-4}$ alkyl,
i) C(Y) (Z)—OH,
j) C(Y) (Z)—O—$C_{1-4}$alkyl
k) $C_{1-6}$ alkyl-$CO_2$—Y, and
l) =O or =S;
wherein Y and Z are each independently H or $C_{1-6}$ alkyl,
$R^6$ and $R^{6'}$ together form =O or =S, or each is independently selected from the group consisting of:
a) hydrogen,
b) hydroxy or lactone,
c) halo,
d) $C_{1-6}$ alkoxy, $C_{1-6}$ alkylthio, $C_{1-6}$ alkyl, or $C_{1-6}$ haloalkyl,
e) CN,
f) $N_3$,
g) $CO_2H$,
h) $CO_2$—$C_{1-4}$ alkyl,
i) C(Y) (Z)—OH,
j) C(Y) (Z)—O—$C_{1-4}$ alkyl, and
k) $C_{1-6}$ alkyl-$CO_2Y$,
wherein Y and Z are each independently H or $C_{1-6}$ alkyl,
Q is:
a) O or S, or
b) N—W, wherein W is:
i) hydrogen,
ii) $C_{1-6}$ alkoxyalkyl, $C_{1-6}$ alkyl, or $C_{1-6}$ haloalkyl
iii) $OC_{1-6}$ alkyl, or $OC_{1-6}$ haloalkyl,
iv) CN,
v) $C_{1-6}$ alkyl,
vi) $C(Y)(Z)C_{1-4}$ alkyl, or
vii) $C_{1-6}$ alkyl-$CO_2$—Z,
wherein Y and Z are each independently H or $C_{1-6}$ alkyl.

Many cannabichromene derivatives are known, and others can be synthesized using methods that are known in the art (see, e.g., U.S. Pat. No. 4,315,862).

In addition to having the indicated substituents, $R^3$ in any of formulas I-V preferably is:

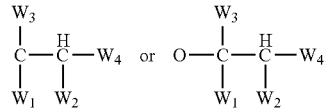

wherein $W_1$ is H, methyl, or ethyl, wherein $W_2$ and $W_3$ are each independently H or methyl, wherein at least one of $W_1$, $W_2$, and $W_3$ is other than H and/or halogenated, and wherein $W_4$ is a $C_{1-4}$ alkyl or haloalkyl, optionally substituted with an aromatic ring. Preferably, $R^3$ is a branched $C_{6-2}$ alkyl group containing at least one double bond (more preferably at position $C_4$-$C_{10}$), and preferably the chain has an odd number of carbon atoms. More preferably, $R^3$ is terminally branched or contains a terminal double bond, and the invention provides compounds according to Formulas I-V having such substituents. More preferably, $R^3$ preferably is dimethylheptyl (DMH) (e.g., 1',1' DMH or 1'R,2'S DMH), dimethylhexyl, or dimethylpentyl. For example, $R^3$ can be a di- tri- or tetramethylpentyl, -hexyl, or -heptyl, etc., chain (e.g., 1,1,5-trimethylhexyl, 1,1,5,5-tetramethylhexyl, or 1,1,5-trimethylhept-4-enyl). In some instances, the $R^3$ substituent can have bulky terminal moieties, for example, methyl, dimethyl, $(CH_2)_{1-6}$ $CON(CH_3)_2$, or $C_{6-12}$ haloalkyl with halogenated terminal carbon atoms (preferably bromine).

In the context of this invention, halogenated alkanes, alkenes, and alkynes can have any number of halogen substitutions. In a preferred embodiment, the halogenated alkane, alkene, or alkyne has at least one halogen on a terminal carbon atom (e.g., $CX_{1-3}$, wherein X is halogen). Alkyl groups (as well as alkenes and alkynes) can be straight chain or branched. Moreover, the compounds can exist as a single stereoisomer or a mixture of stereoisomers (e.g., a racemic mixture), or a single geometric isomer (e.g., E, Z, cis or trans) or a mixture of geometric isomers, all of which are within the scope of the invention.

In carrying out the inventive method, the composition can be delivered to a patient in any amount and over any time course suitable for producing the desired therapeutic effect, and one of skill in the art will be able to determine an acceptable dosing schedule. For example, where the method is employed to treat HIV disease, an optimal dosage can be assessed by assaying the number of circulating viral particles (viral load) and/or CD4+ cell count in response to increasing dosage. Typically, the composition is delivered to a patient between 1 and about 6 times a day, if not continuously through transdermal or time release formulations. However, in some applications, it is appropriate to administer the composition less often. Generally each dose is between about 2 mg/m3 to about 1000 mg/m3, and more preferably about 0.01 mg/kg/day, about 1 mg/kg/day, such as about 1 mg/kg/day to about 10 mg/kg/day, and can be up to about 100 mg/kg/day (e.g., about 250 mg/kg/day). These dosages can be somewhat reduced when the composition is employed in combination with other agents, and especially when the cytochrome $P_{450}$ system is attenuated (e.g., through cannabidiol derivatives), as discussed herein. Moreover, where a selective CB1 antagonist is employed, it can be administered in the same dose or composition as the inventive composition or in a different formulation or dosing schedule. In some applications, it is preferable to begin administering the selective CB1 antagonist prior to (e.g., at least 1-4 days prior to) the composition, to further minimize any residual activation of the CB1 receptor and to prevent degradation of the compound(s) within the composition. Of course, as some patients can develop tolerance to one or more compounds within the composition over the course of treatment, the dosage amount and/or schedule can be adjusted as appropriate. Moreover, the dosage amount and schedule can be reduced as a patient responds favorably to treatment and/or if any toxic side effects are noted.

By virtue of its many effects, the method can be employed to treat many diseases or disorders associated with immune dysfunction in addition to HIV disease. For example, the method can treat autoimmune diseases (e.g., systemic lupus-erythrematosis, Hashimoto's thyroiditis, Grave's disease, myasthenia gravis, rheumatoid arthritis, multiple sclerosis, Guillan-Barre syndrome, glomerulonephritis, polyarteritis nodosa, psoriasis etc.). The method can also treat diseases causing or depending on inflammatory conditions (e.g., Crohn's disease, ulcerative colitis, forms of asthma, cystic fibrosis, Alzheimer's disease, atherosclerosis and associated cardiovascular diseases), and it is particularly effective in combating many neoplastic diseases, microbial (e.g., mycobacterial, fungal) infections, or viral infections, especially HSV, Epstein-Barr virus, Cytomegalovirus, HIV, and hepatitis B and C). The method can also treat abnormal immune responses, abnormal scar formation (e.g., surgical adhesions or keloids), allograft rejection, atherosclerosis and associated heart diseases. Of course, the patient can be any sort of animal (e.g., a monkey, cat, dog, horse, cow, pigs, goat, and sheep, etc.).

Of course, where the method is employed to combat a disease associated with immune dysfunction, other appropriate therapeutic agents can be adjunctively employed as well. For example, the method can include the adjunctive administration of antineoplastics, antitumor agents, antibiotics, antifungals, antivirals (particularly antiretroviral compounds), antihelminthic, and antiparasitic compounds. Exemplary antiviral agents suitable for adjunctive use in the inventive method include abacavir, azidothymidine cidofovir, delavirdine mesylate, didanosine, dideoxycytidine, efavirenz, foscarnet, ganciclovir, indinavir sulfate, lamivudine, nelfinavir mesylate, nevirapine, ritonavir, saquinavir, saquinavir mesylate, stavudine, zalcitabine, etc. In treating tumors or neoplastic growths, suitable adjunctive compounds can include anthracycline antibiotics (such as doxombicin, daunorubicin, carinomycin, N-acetyl adri amycin, rubidazone, 5-imidodaunomycin, and N-acetyldaunomycin, and epirubicin) and plant alkaloids (such as vincristine, vinblastine, etoposide, ellipticine and camptothecin), paclitaxel and docetaxol, mitotane, cisplatin, phenesterine, etc. Anti-inflammatory therapeutic agents suitable for adjunctive use in the present invention include steroids and non-steroidal anti-inflammatory compounds, (such as prednisone, methyl-prednisolone, paramethazone, 11-fludrocortisol or fluorocortisone, triamciniolone, betamethasone and dexamethasone, ibuprofen, piroxicam, beclomethasone; methotrexate, azaribine, etretinate, anthralin, psoralins); salicylates (such as aspirin; and immunosuppresant agents such as cyclosporine). Additional pharmacologic agents suitable for adjunctive use in the inventive method include anesthetics (such as methoxyflurane, isoflurane, enflurane, halothane, and benzocaine); antiulceratives (such as cimetidine); antiseizure medications (such as barbituates; azothioprine (an immunosuppressant and antirheumatic agent); and muscle relaxants (such as dantrolene and diazepam). Moreover, the method can be employed in conjunction with specific antibody therapies or steroid therapies in treating autoimmune diseases. Other pharmacologically-active agents that can be adjunctively employed in conjunction with the composition include other constituents of natural marijuana having antimicrobial or anti-inflammatory activities (e.g., cannabigerol and its derivatives, cannabichromine and its derivatives, cannabinolic acid and its derivatives, cannabidiolic acid and its derivatives, terpenoids, flavanoids (e.g., canniflavin), etc.).

The composition can include biologically active agents, such as lymphokines or cytokines, anti-inflammatory, anti-bacterial, anti-viral, anti-fungal, anti-parasitic, anti-metabolic, anti-inflammatory, vasoactive, anti-neoplastic, bronchoacting, local anesthetic, immunomodulating, enzymatic, hormonal, growth promoting and regenerating agents, as well as neurotransmitters, and cell receptor proteins and ligands, among many other agents. Examples of other biological agents are analgesics (such as acetominophen, anilerdine, aspirin, buprenorphine, butabital, butorphanol, choline salicylate, codeine, dezocine, diclofenac, diflunisal, dihydrocodeine, elcatonin, etodolac, fenoprofen, hydrocodone, hydromorphone, ibuprofen, ketoprofen, ketorolac, levorphanol, magnesium salicylate, meclofenamate, mefenamic acid, meperidine, methadone, methotrimeprazine, morphine, nalbuphine, naproxen, opium, oxycodone, oxymorphone, pentazocine, phenobarbital, propoxyphene, salsalate, sodium salicylate, tramadol and narcotic analgesics in addition to those listed above). Anti-anxiety agents are also useful including alprazolam, bromazepam, buspirone, chlordiazepoxide, chlormezanone, clorazepate, diazepam, halazepam, hydroxyzine, ketazolam, lorazepam, meprobamate, oxazepam and prazepam, among others. Other biologically-active agents include anti-anxiety agents associated with mental depression, such as chlordiazepoxide, amitriptyline, loxapine, maprotiline, and perphenazine, among others. Examples of other active ingredients include anti-inflammatory agents such as non-rheumatic aspirin, choline salicylate, diclofenac, diflunisal, etodolac, fenoprofen, floctafeninc, flurbiprofen, ibuprofen, indomethacin, ketoprofen, lidomide, magnesium salicylate, meclofenamate, mefenamic acid, nabumetone, naproxen, oxaprozin, phenylbutazone, piroxicam, salsalate, sodium salicylate, sulindac, tenoxicam, tiaprofenic acid, thalidomide, linomide, and tolmetin, as well as anti-inflammatories for ocular treatment (such as diclofenac, flurbiprofen, indomethacin, ketorolac, and rimexolone (generally for post-operative treatment)), and anti-inflammatories for non-infectious nasal applications (such as beclomethaxone, budesonide, dexamethasone, flunisolide, triamcinolone, and the like); soporifics (anti-insomnia/sleep inducing agents) such as those utilized for treatment of insomnia, including alprazolam, bromazepam, diazepam, diphenhydramine, doxylamine, estazolam, flurazepam, halazepam, ketazolam, lorazepam, nitrazepam, prazepam quazepam, temazepam, triazolam, zolpidem and sopiclone, among others; sedatives including diphenhydramine, hydroxyzine, methotrimeprazine, promethazine, propofol, melatonin, trimeprazine, and the like; sedatives and agents used for treatment of petit mal, seizures and tremors, among other conditions, such as amitriptyline HCl; chlordiazepoxide, amobarbital; secobarbital, aprobarbital, butabarbital, ethchlorvynol, glutethimide, L-tryptophan, mephobarbital, methohexital sodium salt, midazolam HCl, oxazepam, pentobarbital Na, Phenobarbital, secobarbital sodium salt, thiamylal sodium, and many others. Other active compounds can include agents used in the treatment of head trauma (brain injury/ischemia), such as enadoline HCl (e.g., for treatment of severe head injury), cytoprotective agents, and agents for the treatment of menopause, menopausal symptoms (treatment), e.g., ergotamine, belladonna alkaloids and phenobarbital, for the treatment of menopausal vasomotor symptoms, e.g., clonidine, conjugated estrogens and medroxyprogesterone, estradiol, estradiol cypionate, estradiol valerate, estrogens, conjugated estrogens, esterified estrone, estropipate, and ethinyl estradiol. Examples of agents for treatment of pre menstrual syndrome (PMS) are progesterone, progestin, gonadotrophic releasing hormone, oral contraceptives, danazol, luprolide acetate, vitamin B6; agents for treatment of emotional/psychiatric treatments such as tricyclic antidepressants including amitriptyline hydrochloride (Elavil), perphenazine (Triavil) and doxepin HCl (Sinequan). Examples of tranquilizers, anti-depressants and anti-anxiety agents are diazepam (Valium), lorazepam (Ativan), alprazolam (Xanax), SSRI's (selective Seratonin reuptake inhibitors), fluoxetine hydrochloride (Prozac), sertraline hydrochloride (Zoloft), paroxetine hydrochloride (Paxil), fluvoxamine maleate (Luvox) venlafaxine hydrochloride (Effexor), serotonin, serotonin agonists (Fenfluramine); antibiotics (e.g., fluoroquinolones and tetracycline); antihistamines catabolic steroids; and vasoactive agents (e.g., betablockers and pentoxiphylline (Trental)). Other compounds include cannabinoids such as CT-3 and HU-210.

As mentioned, for use in the inventive method, the compound(s) are incorporated into a pharmacologically-acceptable composition including a suitable carrier, and optionally other inactive or active ingredients. Such compositions are suitable for delivery by a variety of commonly-employed routes of delivery, such as, for example, buccal, sublingual, dermal, intraocular, intraotical, pulmonary, transdermal, intralymphatic, intratumor, intracavitary, intranasal, subcutaneous, implantable, inhalable, intradermal, rectal, 1, transmucosal, intramuscular, intravenous and intraarticular routes, among many others. Depending on the desired manner of application, the composition can include adjuvants, bile salts, biodegradable polymers and co-polymers, buffers, chelating agents, colorants, diluents, emollients, emulsifiers, enzyme inhibitors, hydrogels, hydrophilic agents, lipoproteins and other fatty acid derivatives, liposomes and other micelles, microporous membranes, mucoadhesives, neutral and hydrophobic polymers and co-polymers, particulate systems, perfumes, salt forming acids and bases, semi-permeable membranes, single or multiple enteric coatings, solvents (e.g., alcohols, dimethyl sulfoxide (DMSO), etc.), surfactants, viral envelope proteins, or other ingredients.

In one of its forms, the composition can be an inhalable formulation comprising an aerosol of liquid or solid particles, such as are known in the art. Application of the composition via inhalation can treat bronchial conditions associated with inflammation (e.g., the common cold (rhinovirus), influenza, cystic fibrosis, etc.). This formulation can further comprise additional agents such as preservatives, antioxidants, flavoring agents, volatile oils, buffering agents, dispersants, surfactants, and the like, as are known in the art. Such formulation can also be provided with an inhalant, or in the inhalant, either in unit form or in a form which permits its repetitive use.

The composition can also be a topical formulation (e.g., ointment, cream, lotion, paste, gel, spray, aerosol oil, etc.), wherein the carrier is a diluent for the agent suitable for topical delivery, e.g., petrolatum, lanoline, polyethylene glycols, alcohols and the like, optionally including trans-dermal enhancers. In the topical formulation, the carrier may be in a form suitable for formulating creams, gels, ointments, sprays, aerosols, patches, solutions, suspensions and emulsions.

The composition can also be formulated for oral delivery, for example in the form of capsules, cachets, lozenges, tablets, powder, granules, solutions, suspensions, emulsions, essential oils (particularly hemp seed oil), etc. Such formulations typically include aqueous or non-aqueous liquid solutions and suspensions (e.g., oil-in-water or water-in-oil emulsions). Such oral formulations typically are encased in an enteric coating. Examples of oral formulations are buccal or sub-lingual formulation comprising lozenges which can also comprise flavoring agents and other known ingredients, or pastilles which can also comprise an inert base containing, for example, gelatin, glycerin, sucrose, acacia, and other ingredients and fillers as is known to the practitioner.

The composition can also be a parenteral formulation, such as injectable solutions and suspensions. Typically, such formulations also comprise agents such as anti-oxidants, buffers, anti-bacterial agents, other anti-viral agents such as direct acting inhibitors of replication, and solutes which render the solution or suspension isotonic with the blood of an intended recipient. The solutions or suspensions are typically sterile aqueous or non-aqueous injectable solutions or suspensions, and can also comprise suspending agents and thickening agents. This formulation is generally provided in a sealed ampule or vial.

The composition can also be a slow release formulation, which, when administered or applied to a subject, is capable of releasing a desired amount of the compound(s) over a pre-determined period of time. Alternatively, the composition can be a transdermal formulation, in which the carrier is suitable for facilitating the transdermal delivery of the agent. Examples are aqueous and alcoholic solutions, DMSO, oily solutions and suspensions, and oil-in-water or water-in-oil emulsions. A transdermal formulation can also be an iontophoretic transdermal formulation, in which typically the carrier can be an aqueous and/or alcoholic solution, an oily solution or suspension and an oil-in-water and water-in-oil emulsion. This formulation can further comprise a transdermal transport promoting agent, and be provided in the form of a kit with a transdermal delivery device, preferably an iontophoretic delivery device, many variations of which are known in the art.

Additional formulations of the composition include, but are not limited to an implantable capsule or cartridge (e.g., for tissue implantation), a patch, an implant, or a suppository (e.g., for rectal or transmucosal administration).

Typically, the composition will be distributed, either to physicians or to patients, in an administration kit, and the invention provides such an immunomodulating kit. Typically, such kits include, in separate containers, an administration device (e.g., syringes and needles, inhalators, pills, suppositories, transdermal delivery devices, etc) and a plurality of unit dosages of the composition as described above. In some kits, the composition can be preformulated. Other kits include separate ingredients for formulating the composition. The kit can additionally comprise a carrier or diluent, a case, and instructions for formulating the composition (if applicable) and for employing the appropriate administration device.

As mentioned, compounds according to Formula I have antineoplastic or cytotoxic activity, and the invention provides a method of inhibiting the growth of a neoplasm (e.g., a neoplastic cell or tumor), comprising delivering such a compound to the neoplasm under conditions sufficient for the growth of the neoplasm to be inhibited. Without being bound by any particular theory, resorcinols as described herein can cause DNA cleavage, which can potentially induce apoptosis within neoplastic cells. In this regard, preferably the resorcinol derivative is delivered to the neoplasm under conditions sufficient to potentiate apoptosis. The exact dosing schedule needed to induce apoptosis will depend on the type of compound employed, and whether additional compounds are also employed. In this regard, the method can be delivered adjunctively, in conjunction with the delivery of at least one other antineoplastic agent (such as those set forth above).

In many applications, the method is employed in vivo (e.g., within a patient), such as within a tumor or blood dyscrasia. In some such in vivo applications, the resorcinol derivative is delivered to the neoplasm by introducing it into systemic circulation, such as through the gastric, intestinal, oral, or rectal wall or via intravenous injection. In still other applications where the neoplasm is or comprises a tumor, the resorcinol derivative can be delivered by intratumoral injection. Such mode of delivery can, in some instances, increase the potential local concentration of the compound. For such in vivo applications, the compound can be formulated into a pharmacologically-acceptable composition as indicated herein, as appropriate.

The method can be employed to combat tumor growth, which, while preferable, need not result in elimination of the tumor or decrease in tumor mass. In this regard, the method can be employed to attenuate tumor growth. Such an effect can, for example, make otherwise resistant neoplastic cells more susceptible to other antineoplastic agents, and the method contemplates the adjunctive use of such other compounds, many of which are known in the art (e.g., aldesleukin, altretamine, amifostine, asparaginase, azathioprine, bicalutamide, bicalutamide, bleomycin, busulfan, capecitabine, carboplatin, carmustine, chlorambucil, cisplatin injection, cladribine, cyclophosphamide, cyclosporine o, cytarabine, cytarabine liposome injection, dacarbazine, dactinomycin, daunorubicin, denileukin diftitox, dexrazoxane, docetaxel, doxorubicin, doxorubicin hydro-chloride, estramustine phosphate sodium, etoposide, etoposide phosphate, floxuridine pegaspargase, fludarabine phosphate, flutamide, gemcitabine HCl, goserelin, granisetron hydrochloride, hydroxyurca, idarubicin hydrochloride, ifosfamide, interferon alfa-2a, recombinant, interferon alfa-2b, irinotecan hydrochloride, leucovorin, leuprolide acetate, levamisole, lomustine, L-PAM, L-phenylalanine mustard, mechlorethamine, melphalan, mercaptopurine, methotrexate, mitomycin, mitotane, mitoxantrone hydrochloride, nilutamide, nilutamide, octreotide, ondansetron hydrochloride, paclitaxel, pamidronate disodium, pentostatin, phenylalanine mustard, plicamycin, polifeprosan 20 with carmustine implant, porfimer sodium, procarbazine HCl, rituximab, sargramostim, streptozocin 2-deoxy-2-[[(methylnitrosoamino), tamoxifen citrate, teniposide, testolactone, thioguanine, thiotepa for injection, topotecan hydrochloride, toremifene citrate, trastuzumab, tretinoin, trimetrexate glucuronate, valrubicin, vinblastine sulfate, vincristine sulfate, vinorelbine tartrate, etc.). Moreover, even where tumor growth continues, such attenuation is useful for slowing the progress of the disease, thus permitting greater time for other therapeutic approaches. Indeed, combination therapy may allow for smaller or greater doses of other such antineoplastic agents for shorter or longer durations, thus potentially facilitating increased efficacy and potentially reducing side effects.

EXAMPLES

While one of skilled in the art is fully able to practice the instant invention upon reading the foregoing detailed description, the following examples will help elucidate some of its features. Of course, as these examples are presented for purely illustrative purposes, they should not be used to construe the scope of the invention in a limited manner, but rather should be seen as expanding upon the foregoing description of the invention as a whole.

Example 1

This example demonstrates the synthesis of a compound according to Formula I. A mixture of 2,6-dimethoxyphenol (73.4 g, 0.48 mole), 2,6-dimethyl-2-heptanol (69.0 g, 0.48 mole) and methanesulfonic acid (95 mL) was stirred at 50° C. for 3 h and then at room temperature overnight. The mixture was poured over ice-water (600 mL) with stirring. The mixture was extracted with $CH_2Cl_2$ ($2\times200$ mL). The extracts were washed with water, saturated aqueous $NaHCO_3$, saturated aqueous sodium chloride solution and dried over anhydrous $Na_2SO_4$. The solution was concentrated under reduced pressure to obtain the product as an oil (130 g, 96%). Analysis of this substance (MS (NAB) m/z 281 (MH)'; $^3$H NMR ($CDCl_3$) δ0.80 (d, 6H), 1.0-1.1 (m, 4H), 1.27 (s, 6H), 1.40-1.60 (m, 3H), 3.89 (s, 6H), 5.36 (s, 1H), 6.54 (s, 2H)) revealed it to be 4-(1,1,5-trimethylhexyl)-2,6-dimethoxy phenol:

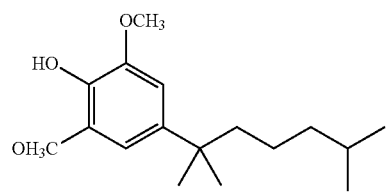

Example 2

This example demonstrates the synthesis of a compound according to Formula I. A solution of crude 4-(1,1,5-trimethylhexyl)-4,6, dimethoxyphenol from Example 1 (130 g, 0.46 mole) in dry $CCl_4$ (100 mL) was cooled in ice-bath and diethyl phosphite (70 mL, 0.54 mole) was added. To the stirred mixture triethylamine (75 mL, 0.54 mole) was added drop-wise at such a rate as to maintain the temperature of the reaction mixture below 10° C. The reaction mixture was stirred in the ice-bath for 2 h and at room temperature overnight. The mixture was then diluted with $CH_2Cl_2$ (200 mL), washed with water, 4N aqueous NaOH (100 mL), 1N aqueous HCl (125 mL), water and saturated aqueous sodium chloride solution. The extracts were dried over anhydrous $Na_2SO_4$ and concentrated under reduced pressure. The crude product was purified by chromatography over a column of silica using cyclohexane:EtOAc (7:1 to 3:1 gradient) as the eluent to obtain 103 g (54%) of the product as a colorless waxy oil. Analysis of this substance (MS (FAB) m/z 417 (MH)'. $^3$H NMR ($CDCl_3$) δ0.81 (d, 6H), 1.0-1.1 (m, 4H), 1.26 (s, 6H), 1.35-1.6 (m, 9H), 3.86 (s, 6H), 4.25-4.38 (m, 4H), 6.53 (s, 2H)) revealed it to be 4-(1,1,5-trimethylhexyl)-2,6-dimethoxyphenyl diethyl phosphate:

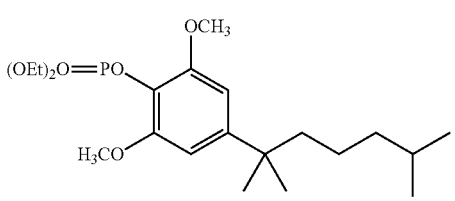

Example 3

This example demonstrates the synthesis of a compound according to Formula I. A solution of 4-(1,1,5-trimethylhexyl)-2,6-dimethoxyphenyl diethyl phosphate from Example 2 (82 g, 0.197 mole) in Et$_2$O (175 mL) and THF (35 mL) was added slowly to liquid ammonia (450 mL) contained in a 3-neck vessel fitted with mechanical stirrer, thermometer, dry ice condenser and a pressure equalizing addition funnel while adding small freshly cut pieces of lithium wire (2.8 g, 0.40 g-atom) at such a rate as to maintain a blue color. The reaction mixture was stirred further for an hour and then quenched by the addition of saturated aqueous NH$_4$Cl (22 mL). Ether (220 mL) was added and the ammonia was allowed to evaporate overnight. The residue was treated with water (220 mL). The layers were separated and the ether layer was washed with 4N NaOH (200 mL), water (2×200 mL) and saturated aqueous sodium chloride solution. The organic extracts were dried (MgSO$_4$) and concentrated under reduced pressure. The crude product was purified by chromatography over a column of silica using cyclohexane:EtOAc (95:5) as the eluent to obtain 43 g (83%) of the product as a colorless oil. Analysis of this substance (MS (FAB) m/z 265 (MH)'; $^3$H NMR (CDCl$_3$) δ0.80 (d, 6H), 1.00-1.10 (m, 4H), 1.26 (s, 6H), 1.4-1.6 (m, 3H), 3.79 (s, 6H), 6.30 (m, 1H), 6.49 (m, 2H)) revealed it to be 4-(1,1,5-trimethylhexyl)-2,6-dimethoxybenzene:

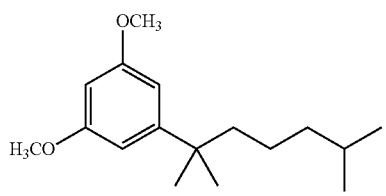 [SMILES: COc1cc(OC)cc(C(C)(C)CCCC(C)C)c1]

Example 4

This example demonstrates the synthesis of a compound according to Formula I. A solution of 4-(1,1,5-trimethylhexyl)-2,6-dimethoxybenzene from Example 3 (10 g, 0.038 mole) in anhydrous CH$_2$Cl$_2$ (100 mL) was cooled in ice-bath and was treated dropwise with a solution of boron tribromide in CH$_2$Cl$_2$ (100 mL of 1M solution, 0.10 mole) over a period of 1 h. The mixture was stirred in the cold bath for 2 h and, then at room temperature overnight. The reaction mixture was cooled in ice-bath and cautiously treated with water (100 mL). The resulting mixture was diluted with CH$_2$Cl$_2$ (100 mL) and treated with half-saturated aqueous sodium bicarbonate solution. The layers were separated, the organic layer was concentrated to half volume under reduced pressure and extracted with 2N aqueous NaOH (2×75 mL). The aqueous alkaline extract was cooled and acidified to pH 3.0 with 1N aqueous HCl. The acidified mixture was extracted with Et$_2$O (2×100 mL). The ether layer was washed with saturated aqueous sodium chloride solution, dried over anhydrous MgSO$_4$ and concentrated under reduced pressure. The crude product thus obtained was purified by chromatography over a column of silica using cyclohexane:EtOAc (8:1 to 4:1 gradient) as the eluent to obtain 8.0 g (90%) of the product as colorless crystalline solid. Analysis of this substance (Mp 95-96° C. MS (FAB) m/z 237 (MH)'; $^1$H NMR (CDCl$_3$) δ0.80 (d, 6H), 1.00-1.10 (m, 4H), 1.23 (s, 6H), 1.40-1.58 (m, 3H), 4.65 (s, 2H), 6.17 (m, 1H), 6.38 (m, 2H)) revealed it to be 4-(1,1,5-trimethylhexyl) resorcinol:

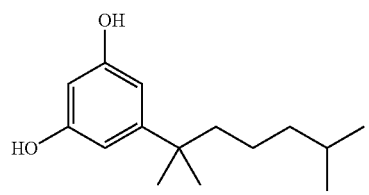 [SMILES: CC(C)CCCC(C)(C)c1cc(O)cc(O)c1]

Example 5

This example demonstrates the synthesis of a compound according to Formula I. A solution of 4-(1,1,5-trimethylhexyl) resorcinol from Example 4 (2 g, 0.0076 mole) in anhydrous CH$_2$Cl$_2$ (10 mL) was cooled in ice-bath and was treated dropwise with a solution of boron tribromide in CH$_2$Cl$_2$ (2.6 mL of 1M solution, 0.0026 mole). The mixture was stirred in the cold bath for 2 h and then at room temperature overnight. The mixture was cooled in ice-bath and cautiously treated with water (10 mL) followed by saturated aqueous sodium bicarbonate (5 mL). The organic layer was separated, dried over MgSO$_4$ and concentrated under reduced pressure. The residue was purified by chromatography over a column of silica using cyclohexane:EtOAc (8:1 to 4:1 gradient) as the eluent to obtain 0.364 g (19%) of the product as a colorless oil. Analysis of this substance (MS (FAB) m/z 251 (MH)'; $^1$H NMR (CDCl$_3$) δ 0.80 (d, 6H), 1.00-1.10 (m, 4H), 1.24 (s, 6H), 1.4-1.6 (m, 3H), 3.78 (s, 3H), 4.67 (s, 1H), 6.23 (m, 1H), 6.40 (m, 1H), 6.47 (m, 1H)) revealed it to be 3-methoxy-5-(1,1,5-trimethylhexyl)phenol

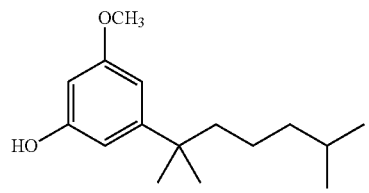 [SMILES: COc1cc(O)cc(C(C)(C)CCCC(C)C)c1]

Example 6

This example demonstrates the antiviral activity of several compounds according to the invention.

Compounds. Compounds indicated in Table 1 were prepared as varying concentrations in SDMSA and used fresh.

Latently Infected Cells. 5×10$^3$ Ul cells (obtained from the AIDS Research and Reference Reagent Program, Bethesda, Md.) were plated in 96-well plates with media with or without 5 ng/ml TNFα and a test compound. After 3 to 6 days incubation, the supernatants and cells were assessed PBMC Isolation and Blasting. Peripheral blood mononuclear cells (PBMC) obtained from healthy HIV- and hepatitis-negative patients were washed to remove residual gradient separation material. The washed cells were then counted, and their viability assessed. Following this initial preparation, the cells are suspended in RPMI 1640 medium supplemented with 15% inactivated fetal bovine serum, 2 mM L-glutamine, 100 U/ml penicillin, 100 µg/ml streptomycin, and 10 µg/ml gentamycin with 2 µg/ml PHA at 1×10$^6$ cells/ml. Following a 2 to 3 day incubation (37° C., 5% $CO_2$), the cells were collected by centrifugation, washed, and resuspended in the same medium, supplemented with recombinant IL-2. The cultures were then maintained until use by ½ volume change with fresh IL-12 containing medium every 3 days.

PBMC Assay. When ready for use, PBMCs from a minimum of two donors that have been blasted with PHA and IL-1 were mixed, counted, and viability determined by trypan blue exclusion. The cells were then resuspended in 1×10 cells/ml in RPMI 1640 supplemented with 15% fetal bovine serum (heat inactivated), 2 mM L-glutamine, 100 U/ml penicillin, 100 µg/ml streptomycin, 10 µg/ml gentamycin and IL-2 (20 U/ml). 50 µl of cells were then distributed to the inner 60 wells of a 96 well plate. Each plate contains cell control wells (cells only), virus control wells (cells plus virus), drug toxicity control wells (cells plus test compound), drug colorimetric control wells (drug only) as well as experimental wells (drug plus cells plus virus). Diluted compounds were then added to the microliter plate followed by the appropriate pre-titered strain of HIV-1. All samples were assayed in triplicate with a sister plate for the determination of compound toxicity. The final volume per well was 200 µl. The assay was incubated for 7 days at 37° C., 5% $CO_2$, after which supernatants were collected for analysis of RT activity and sister plates for assessment of cell viability.

Monocyte Isolation and Culture. Peripheral blood monocytes (PBM) were obtained from healthy HIV- and hepatitis-negative donors by ficoll hypaque purification (optionally using recombinant IFNγ. After 7 days, the cultures were washed to remove non adherent cells, and test compounds were added followed by HIV-1. Cultures were washed a final time by media removal 24 hours post infection, fresh test compound was added, and the cultures continued for an additional seven days. Virus replication was then measured by expression of supernatant p24 antigen by commercially available ELISA assays. AZT was used as a positive control run in parallel with each determination.

XTT Staining for Viability. Absence of toxicity was assessed by reduction of 2,3-bis(2-methoxy-4-nitro-5-sulfophenyl)-5-[(phenylamino)carbonyl]2H-tetrazolium hydroxide (XXT). 50 µl of a solution containing 1 mg/ml XTT and 0.06 µg/ml phenazine methanesulfate (PMS) was added per well, and the plate was incubated for 4 hours at 37° C. Adhesive plate sealers were used in place of the lids so that the sealed plates could be inverted several times to mix the soluble reaction product. Following this incubation, the plates were read spectrophotometrically at 450 nm to assess the degree of reduction product.

Analysis of p24. Viral protein production (p24) was assessed by standard ELISA.Reverse Transcriptase Assay. HIV reverse transcriptase was measured in cell free supernatants. Titrated TTP was resuspended in distilled $H_2O$ at 5 Ci/ml. Poly rA and oligo dT were prepared as a stock solution which was kept at −20° C. The RT reaction buffer (125 µl 1M EGTA, 125 µl d$H_2O$, 110 µl 10% SDS, 50 µl 1M Tris (pH 7.4), 50 µl 1M DTT, and 40 Ml 1M $MgCl_2$) was prepared fresh. The three solutions were then mixed together in a ratio of 2 parts TTP, 1 part PolyrA:oligo dT, and 1 part buffer. Ten µl of this reaction mixture was then placed in a round bottom microliter plate, and 15 µl of virus-containing supernatant was added. The plate was incubated at 37° C. in a water bath with a solid support for 60 minutes. Following the reaction, the volume was spotted onto pieces of DE81 paper, washed 5 times for 5 minutes each in a 5% sodium phosphate buffer, 2 times for 1 minute in distilled water, 2 times for 1 minute each in 70% ethanol, and then dried. Opti-Fluoro was then added to each sample and incorporated radioactivity was quantified using a scintillation counter.

Data Analysis. $IC_{50}$ (i.e., 50% inhibition of virus replication), $TC_{50}$ (50% cytotoxicity), and a selectivity index ($SI=IC_{50}/TC_{50}$) were calculated for each assay. Pooled data for all compounds tested are presented in Table 1. The results indicate that 11-nor-A9-tetrahydrocannabidinol-9-carboxylic acid, cannabidiol, and olivitol, 5-(1,1,5-trimethylhexyl) resorcinol, and 5-(1,1,5-trimethylhexyl)-2,6-dimethoxyphenol exhibited moderate antiviral activity. The antiviral activity of olivitol was more pronounced in the PBMCs and TNFα induced Ul cells than in monocytes/macrophages or uninduced Ul cells. Particularly with reference to the cannabinoids, these results are surprising, given observations that some such compounds can enhance, rather than suppress HIV replication (see, e.g., Noe et al., Chapter 25 in *Drug of Abuse, Immunomodullation and AIDS*, Friedman et al., Ed., (Plenum Press, NY 1998)).

Example 7

This example demonstrates the antineoplastic activity of compounds according to Formula 1.

Cell Lines. Cell lines indicated in table 2 were propagated under sterile conditions in RPMI 1640 or DMEM with 10% fetal calf serum, 2 mM L-glutamine, and sodium bicarbonate ("complete medium") and incubated at 37° C. 5% $CO_2$ and 95% humidity. Each cell line was subcultured once or twice weekly, and they were periodically screened for mycoplasma contamination (positive cultures were cured over three passages with antibiotic). Only cultures free of mycoplasma were used for antineoplastic assessment.

Antineoplastic Assessment. Cells from each cell line were harvested, pelleted to remove the media, and then suspended in fresh complete medium. The cell count was determined and viability was measured with propidium iodide staining. The cells were adjusted with complete medium to a density of $5×10^3$ cells/ml. Tissue culture plates were seeded with 100 µl samples of each cell line, and the plates were incubated overnight to allow for cell anchorage and acclimation.

Following acclimation, the compounds indicated in table 2 were diluted in complete medium. A range of eight concentrations was used to treat the cell cultures. For each dilution, eight wells are each treated with 100 µl of dosing solution. Each culture plate contains a cell control (8 wells, mock treated with complete medium), a medium control (7 wells with medium used to subtract out signal generated by media conditions), a solvent control (8 wells), and an air blank (1 well) for calibrating the plate reader. Each cell line was also treated with a single dose of doxorubicin (1 µM, eight wells) as a positive control for cytotoxicity. Once dosing was completed, the cells were incubated at 37° C. in 5% $CO_2$ and 95% humidity.

Five days after treatment, the cells were analyzed for antineoplastic effects using the SRB assay to calculate $IC_{50}$ for each treatment. The results are presented in Table 2. The results indicate that 5-(26-dimethyl-2-heptyl)resorcinol exhibited an $IC_{50}$ of 77-95 µM in six cell lines, indicating that such compounds have antineoplastic effects.

INCORPORATION BY REFERENCE

All sources (e.g., inventor's certificates, patent applications, patents, printed-publications, repository accessions or records, utility models, world-wide web pages, and the like) referred to or cited anywhere in this document or in any drawing, Sequence Listing, or Statement filed concurrently herewith are hereby incorporated into and made part of this specification by such reference thereto, as is the priority application and International Patent Application PCT/US00/07629, which was published as WO 00/56303.

Guide to Interpretation

The foregoing is an integrated description of the invention as a whole, not merely of any particular element of facet thereof. The description describes "preferred embodiments" of this invention, including the best mode known to the inventors for carrying it out. Of course, upon reading the foregoing description, variations of those preferred embodiments will become obvious to those of ordinary skill in the art. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

As used in the foregoing description and in the following claims, singular indicators (e.g., "a" or "one") include the plural, unless otherwise indicated. Recitation of a range of discontinuous values is intended to serve as a shorthand method of referring individually to each separate value falling within the range, and each separate value is incorporated into the specification as if it were individually listed. As regards the claims in particular, the term "consisting essentially of" indicates that unlisted ingredients or steps that do not materially affect the basic and novel properties of the invention can be employed in addition to the specifically recited ingredients or steps. In contrast, the terms "comprising" or "having" indicate that any ingredients or steps can be present in addition to those recited. The term "consisting of" indicates that only the recited ingredients or steps are present, but does not foreclose the possibility that equivalents of the ingredients or steps can substitute for those specifically recited.

TABLE 1

| Compound | Monocyte/macrophage assay with HIV-1 (p24) | | | PBMC HIV-1 (RT) | | | TNF induced UI cells (RT) | | |
|---|---|---|---|---|---|---|---|---|---|
| | $IC_{50}$ | $TC_{50}$ | TI | $IC_{50}$ | $TC_{50}$ | TI | $IC_{50}$ | $TC_{50}$ | TI |
| AZT (µM) | 0.001 | >4 | >4000 | 0.0021 | >4 | >1904 | — | — | — |
| | 0.0056 | | | 0.0056 | >4 | 714.2 | | | |
| | 0.0061 | >4 | 655.7 | 0.0034 | >4 | 1176 | | | |
| | | | | 0.099 | >10 | >101.0 | | | |
| DdC (µM) | 0.0028 | >10 | >3571 | 0.0876 | >10 | 114 | — | — | — |
| Cannabinol (µg/ml) | 7.7 | 13.07 | 1.7 | 6.91 | 7.66 | 1.11 | 5.14 | 5.26 | 1.0 |
| Cannabidiol (µg/ml) | 8.18 | 22.87 | 2.8 | 1.52 | 7.76 | 5.11 | 2.76 | 7.8 | 2.8 |
| 11-nor-Δ9-tetrahydrocannabidinol-9-carboxylic acid (µg/ml) | 7.79 | 76.73 | 9.8 | 39.09 | 71.1 | 1.82 | 6.69 | 23.71 | 3.55 |
| Δ8 tetrahydrocannabinol (µg/ml) | >0.1 | >0.1 | NA | 0.08 | >0.1 | >1.25 | 0.06 | >0.1 | >1.667 |
| Δ9 tetrahydrocannabinaol (µg/ml) | >0.1 | >0.1 | NA | 0.07 | >0.1 | 1.43 | 0.06 | 0.088 | 1.47 |
| EtOH (%) | 0.06 | >1 | >1.67 | >0.1 | >0.1 | NA | >0.1 | >0.1 | NA |
| Olivitol (µM) | 63.7 | 75.9 | 1.19 | 16.9 | >100 | 5.9 | 22.5 | 77.5 | 3.45 |
| Resorciol (µM) | NA | NA | NA | >200 | >200 | — | NA | NA | NA |
| Orcinol (µM) | NA | NA | NA | >200 | >200 | — | NA | NA | NA |
| 5-(1,1,5-trimethylhexyl) resorcinol (µM) | NA | NA | NA | 14.8 | 44.6 | 3 | NA | NA | NA |
| 5-(1,1,5-trimethylhexyl)-2,6-dimethoxyphenol (µM) | NA | NA | NA | 15.8 | 50.9 | 3.2 | NA | NA | NA |
| 5-(1,1,5-trimethylhexyl)-2,6-dimethoxybenzene (µM) | NA | NA | NA | >200 | >200 | — | NA | NA | NA |
| 3-methoxy-5-(1,1,5-trimethylhexyl)phenol (µM) | NA | NA | NA | 39.9 | 46.4 | 1.2 | NA | NA | NA |

TABLE 2

| | $IC_{50}$ Values in µg/ml ($IC_{50}$ Molar Values) | | | | | | |
|---|---|---|---|---|---|---|---|
| | SNB-7 (CNS) | DLD-1 (colon) | NCI-H23 (lung) | ZR-75-1 (mammary) | LOX IMVI (melanoma) | PC-3 (prostate) | CAKI-1 (renal) |
| 5-(2,6-dimethy-2-heptyl)resorcinol | $2.2 \times 10^1$ ($9.5 \times 10^{-5}$) | $2.1 \times 10^1$ ($9.0 \times 10^{-5}$) | $1.8 \times 10^1$ ($7.7 \times 10^{-5}$) | $1.9 \times 10^1$ ($8.1 \times 10^{-5}$) | NA | $2.0 \times 10^1$ ($8.4 \times 10^{-5}$) | $2.2 \times 10^1$ ($9.3 \times 10^{-5}$) |
| Olivetol | $4.0 \times 10^1$ ($2.2 \times 10^{-4}$) | $4.2 \times 10^1$ ($2.3 \times 10^{-4}$) | $3.3 \times 10^1$ ($1.8 \times 10^{-4}$) | $3.6 \times 10^1$ ($2.0 \times 10^{-4}$) | $4.4 \times 10^1$ ($2.4 \times 10^{-4}$) | $3.7 \times 10^1$ ($2.0 \times 10^{-4}$) | $4.0 \times 10^1$ ($2.2 \times 10^{-4}$) |

I claim:

1. A method of treatment of HIV, Simian Immuno deficiency Virus, Feline Immunodeficiency Virus and influenza, the method comprising administering to a subject in need thereof a therapeutically effective dose of a cannabinoid derivative having the formula:

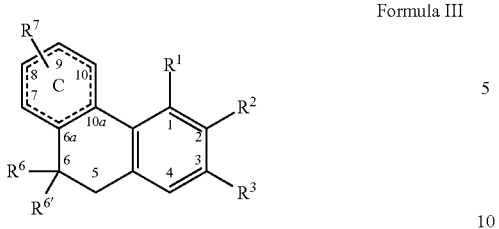
Formula III
wherein,
$R^1$ is H;
$R^2$ is H;
$R^3$ is $(W)_m$—Y—$(Z)_n$, wherein
W is a $C_{5-12}$ straight or branched alkyl,
Y is a bond,
Z is a $C_{5-12}$ alkyl, and wherein
m and n are different, and each is either 0 or 1;
$R^6$ and $R^{6'}$ each is $C_1$ alkyl;
$R^7$ is $C_1$ alkyl;
Q is O; and the dashed line of Ring C represents a double bond at position Δ8-9.
* * * * *